(12) United States Patent
Jones et al.

(10) Patent No.: US 8,263,623 B2
(45) Date of Patent: Sep. 11, 2012

(54) TRIAZOL DERIVATIVES USEFUL FOR THE TREATMENT OF DISEASES

(75) Inventors: Lyn Howard Jones, Sandwich (GB); Dannielle Frances Roberts, Sandwich (GB); Ross Sinclair Strang, Sandwich (GB)

(73) Assignee: Pfizer Inc., New York, NY (US)

( * ) Notice: Subject to any disclaimer, the term of this patent is extended or adjusted under 35 U.S.C. 154(b) by 507 days.

(21) Appl. No.: 12/496,054

(22) Filed: Jul. 1, 2009

(65) Prior Publication Data
US 2010/0010040 A1  Jan. 14, 2010

Related U.S. Application Data

(60) Provisional application No. 61/079,837, filed on Jul. 11, 2008.

(51) Int. Cl.
*A61K 31/04* (2006.01)
*C07D 215/38* (2006.01)

(52) U.S. Cl. .................. 514/312; 546/159; 546/163
(58) Field of Classification Search .................. 546/159, 546/163; 514/312
See application file for complete search history.

(56) References Cited

U.S. PATENT DOCUMENTS

| 2005/0171147 A1 | 8/2005 | Brown et al. | 514/310 |
| 2005/0222128 A1 | 10/2005 | Brown et al. | 514/218 |

FOREIGN PATENT DOCUMENTS

| EP | 1460064 | 9/2004 |
| WO | WO 9633973 | 10/1996 |
| WO | WO 97/30994 | 8/1997 |
| WO | WO 0104118 | 1/2001 |
| WO | WO 02053564 | 7/2002 |
| WO | WO 03057694 | 7/2003 |
| WO | WO 2004052857 | 6/2004 |
| WO | WO 2004/074246 | 9/2004 |
| WO | WO 2004/074276 | 9/2004 |
| WO | WO 2004/106333 | 9/2004 |
| WO | WO 2004/089892 | 10/2004 |
| WO | WO 2005092840 | 10/2005 |
| WO | WO 2006048225 | 5/2006 |
| WO | WO 2007/017669 | 2/2007 |
| WO | WO 2008/023157 | 2/2008 |

OTHER PUBLICATIONS

Bradsher et al., Journal of Organic Chemistry, 46(22), pp. 4608-4610, 1981.
Jeffries et al., Journal of Organic Chemistry, 46(14), pp. 2885-2889, 1981.
Buehler et al., Journal of Organic Chemistry, 26, pp. 1573-1577, 1961.
Chimica Therapeutica, 4, pp. 238-245, 1966.
Roxburgh et al., Journal of Medicinal Chemistry, 44(20), pp. 3244-3253, 2001.
Saunders, J., et al., Novel Quinuclidine-Based Ligands for the Muscarinic Cholinergic Receptor, J. Med. Chem., vol. 33, 1128-1138 (1990).

*Primary Examiner* — D M Seaman
*(74) Attorney, Agent, or Firm* — A. Dean Olson

(57) ABSTRACT

The invention relates to compounds of formula (1)

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

18 Claims, 1 Drawing Sheet

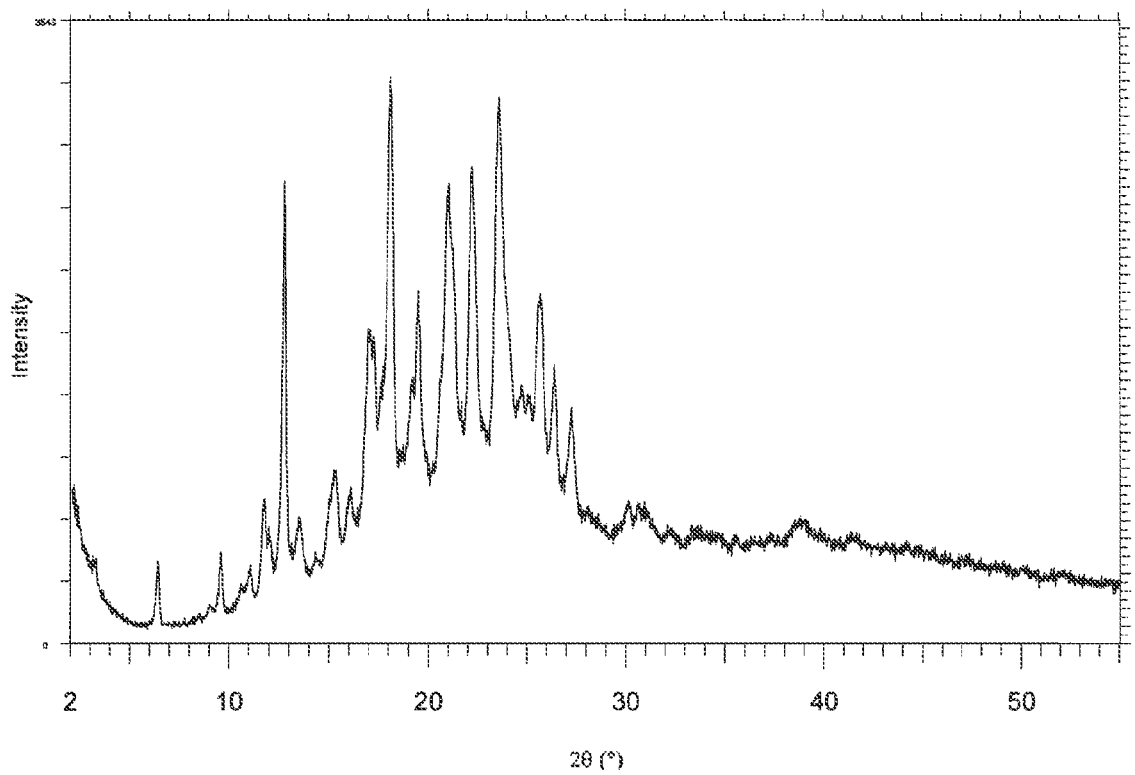

TRIAZOL DERIVATIVES USEFUL FOR THE TREATMENT OF DISEASES

This invention relates to compounds of general formula (1):

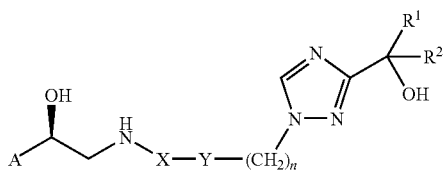

in which A, X, Y, n, $R^1$ and $R^2$ have the meanings indicated below, and to processes and intermediates for the preparation of, compositions containing and the uses of such derivatives.

$\beta_2$ adrenergic agonists and cholinergic muscarinic antagonists are well-established therapeutic agents for the treatment of obstructive respiratory diseases such as COPD and Asthma. Currently used inhaled $\beta_2$ agonists include both short acting agents such as salbutamol (q.i.d.), and terbutaline (t.i.d) and longer acting agents such as salmeterol and formoterol (b.i.d.) and produce bronchodilation via stimulation of adrenergic receptors on airway smooth muscle. Inhaled muscarinic antagonists in clinical use include the short acting ipratropium bromide (q.i.d.), oxitropium bromide (q.i.d) and the long acting tiotropium (q.d.). Muscarinic antagonists produce bronchodilation by inhibiting the cholinergic tone of airways primarily by antagonising the action of acetylcholine on muscarinic receptors present on airway smooth muscle. A number of published studies have demonstrated that the combined administration of inhaled $\beta_2$ agonists with inhaled muscarinic antagonists (whether short or long acting) to patients with obstructive lung disease results in superior improvements in lung function, symptoms and quality of life measures compared to patients receiving either single class of agent alone. Studies to date have been restricted to combination studies with single pharmacology agents, however combination of both pharmacologies within a single molecule would be desirable as this could yield increased bronchodilator efficacy with similar therapeutic index to the single agents or similar efficacy with superior therapeutic index. In addition, combining both pharmacologies in a single molecule would allow the potential for combination with anti-inflammatory agents thus giving a triple therapy from a single inhaler.

Accordingly, there is a need for alternative compounds active as beta 2 receptor agonists and muscarinic antagonists, being suitable for the treatment of respiratory diseases, preferably by the inhalation route. Such compounds would have an appropriate pharmacological profile, for example in term of potency, pharmacokinetics or duration of action. In addition, as these compounds may be used for the treatment of chronic diseases, such as asthma or COPD, they would preferably have a low potential for interaction with co-administered compounds.

The invention relates to the compounds of general formula (1):

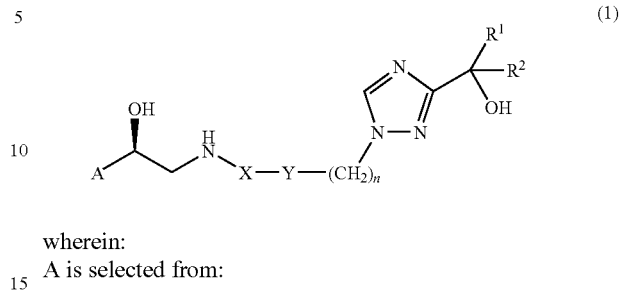

wherein:
A is selected from:

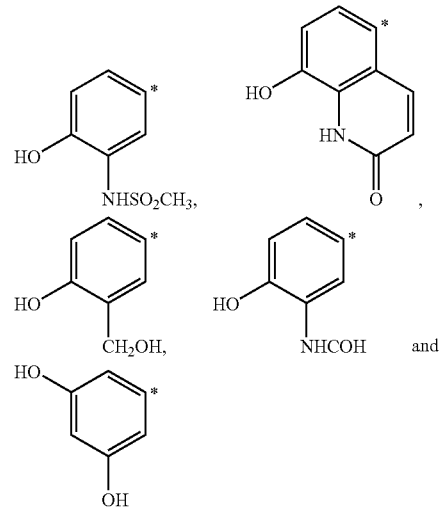

wherein * represent the attachment point of A to the carbon bearing the hydroxy;
X is —$(CH_2)_m$— where m is an integer comprised between 7 to 12 inclusive, or is of formula:

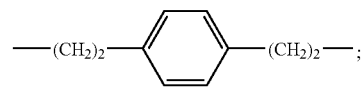

Y is selected from

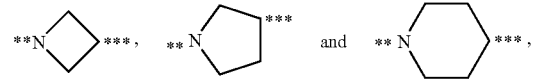

wherein  and * represent the attachment points, ** being linked to X;
n is 0 or 1;
$R^1$ is selected from cyclopentyl, cyclohexyl, phenyl, furanyl and thiophenyl; and,
$R^2$ is selected from phenyl, furanyl and thiophenyl;
or the pharmaceutically acceptable salts thereof, or the pharmaceutically acceptable solvates of said compounds or salts.

The compounds of formula (1) are β2 adrenergic receptor agonists and muscarinic receptor antagonists that are particularly useful for the treatment of diseases and/or conditions involving said receptors, by showing excellent potency, in particular when administered via the inhalation route.

Compounds of formula (1) may be prepared in a variety of ways. The routes below illustrate one such way of preparing these compounds, in which A, X, Y, n, $R^1$ and $R^2$ are as previously defined for the compounds of the formula (1) unless otherwise stated. The skilled person will appreciate that other routes may be equally as practicable.

(1)

The amine derivative of the formula (1):

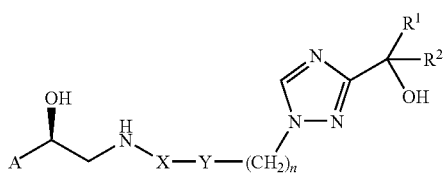

may be prepared by reaction of an amine of formula (2):

(2)

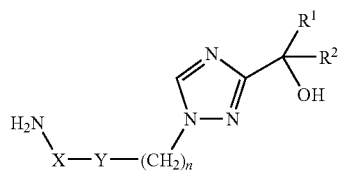

with a bromide of formula (3):

(3)

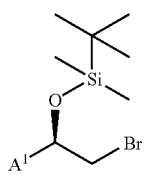

where $A^1$ represents A protected with a suitable phenol protecting group such as benzyl.

In a typical procedure, the amine of formula (2) is reacted with a bromide of formula (3) optionally in the presence of a solvent or mixture of solvents (e.g. dimethyl sulphoxide, toluene, N,N-dimethylformamide, propionitrile, acetonitrile, butyronitrile, dichloromethane), optionally in the presence of a suitable base (e.g. triethylamine, diisopropylethylamine, potassium carbonate, sodium hydrogen carbonate), at a temperature comprised between 80° C. and 120° C., for 12 to 72 hours. The protecting groups such as tert-butyldimethylsilyl and benzyl can then be removed using standard methodology for cleaving oxygen protecting groups such as those found in the text book T. W. Greene, Protective Groups in Organic Synthesis (Wiley-Interscience Publication, 1981).

Compounds of formula (3) where $A^1$ is represented below may be prepared according to the methods disclosed in the following references:

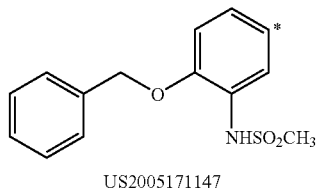

US2005171147

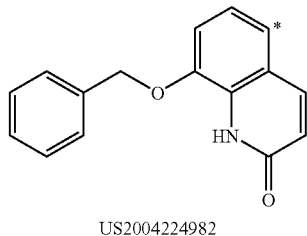

US2004224982

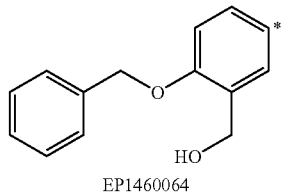

EP1460064

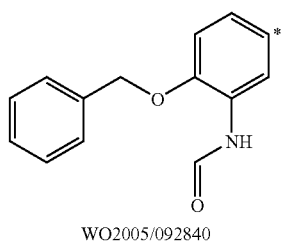

WO2005/092840

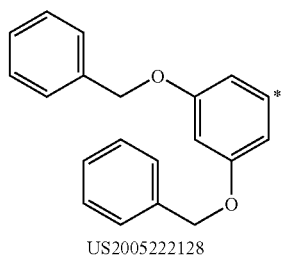

US2005222128

The amine of formula (2) may be prepared from the corresponding protected amine of formula (4):

(4)

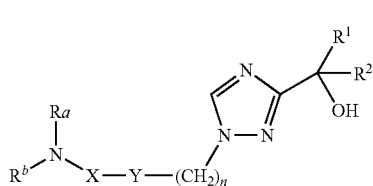

where $R^a$ and $R^b$ represent suitable protecting groups such as tert-butoxycarbonyl or together represent phthalimide.

In a typical procedure, the amine of formula (4) is deprotected using standard methodology for cleaving nitrogen protecting groups such as those found in the text book T. W. Greene, Protective Groups in Organic Synthesis (Wiley-Interscience Publication, 1981).

The amine of formula (4) may be prepared by reacting the corresponding amine of formula (5):

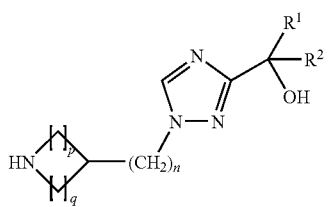
(5)

where p and q are independently selected from 1 or 2, with a compound of formula (6):

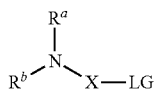
(6)

wherein $R^a$ and $R^b$ are as previously defined and LG is a suitable leaving group such as bromide or mesylate In a typical procedure, the amine of formula (5) is reacted with a compound of formula (6) in a suitable solvent (e.g. dimethyl sulphoxide, toluene, N,N-dimethylformamide, propionitrile, acetonitrile, methyl ethyl ketone), in the presence of a suitable base (e.g. triethylamine, diisopropylethylamine) and optionally in the presence of a nucleophilic additive (e.g. sodium iodide) at a temperature comprised between 50° C. and 90° C., for 18 to 48 hours.

The compounds of formula (6) where LG is bromide may be prepared by reacting the corresponding amine nucleophiles $R^aR^bNH$ with the corresponding dibromide of formula (7):

Br—X—Br (7)

In a typical procedure, phthalimide or di-tert-butyl iminodicarboxylate ($R^aR^bNH$) is reacted with a suitable base such as sodium hydride (60% dispersion in oil), in a suitable solvent such as N,N-dimethylformamide or tetrahydrofuran, at a temperature comprised between 0° C. and room temperature for up to 1 hour, followed by addition of the dibromide of formula (7), at a temperature comprised between 0° C. and 150° C., for 6-48 hours.

The amines of formula $R^aR^bNH$ are commercially available.

Compounds of formula (7) where X is $—(CH_2)_m—$ are commercially available.

Compounds of formula (7) where X is of formula:

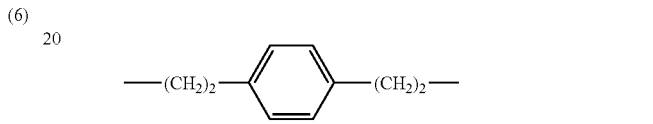

may be prepared as described in Journal of Organic Chemistry, 46(22), 4608-10; 1981.

Alternatively, compounds of formula (6) where $R^a$ and $R^b$ together represent phthalimide and X is of formula:

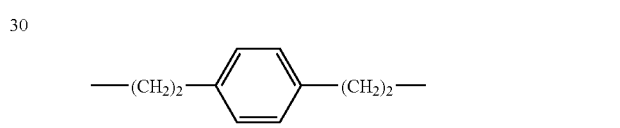

may be prepared as described in scheme 1 below:

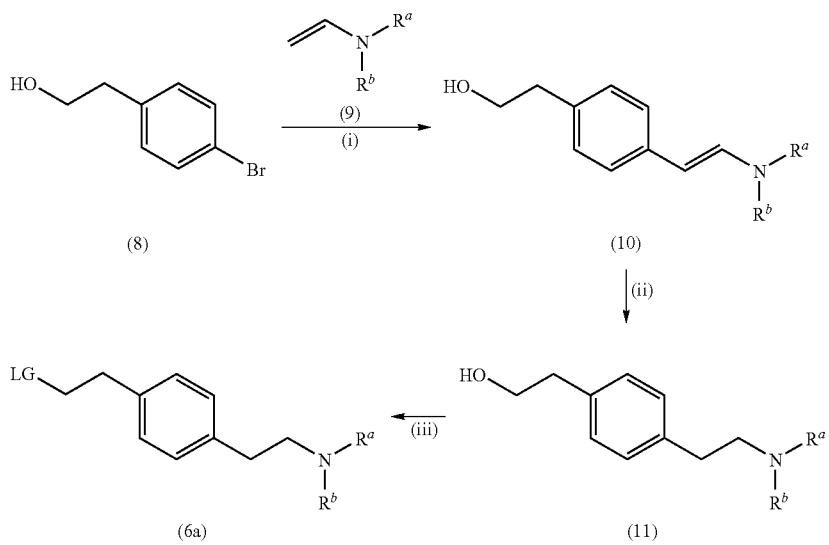

Scheme 1 wherein $R^a$ and $R^b$ together represent phthalimide.

Compounds of formula (8) and (9) are commercially available.

Compound of formula (10) may be prepared from compounds of formula (8) and (9) by Heck reaction (process step In addition to their utility for the preparation of the compounds of formula (1), the compounds of formula (5) may also be used as muscarinic antagonists. In particular they may be useful for the treatment of diseases which can be alleviated by the modulation of the activity of the muscarinic receptor.

(i)). Typical conditions comprise reaction of compound (8) with compound (9), tri-o-tolylphosphine, palladium(II)acetate and a suitable base such as diisopropylethylamine, in a suitable solvent such as acetonitrile, at 90° C. for 21 hours.

Compound of formula (11) may be prepared from compound of formula (10) by hydrogenation (process step (ii)). Typical conditions comprise reaction of compound (10) with ammonium formate and 30% palladium hydroxide on carbon, in suitable solvents such as ethyl acetate and ethanol, at 80° C. for 18 hours. Alternative conditions comprise reaction of compound (10) with hydrogen gas and rhodium tris(triphenylphosphine)chloride, in suitable solvents such as ethyl acetate and ethanol, at 20 psi and room temperature for 24 hours.

Compound of formula (6a) where LG is bromide may be prepared from compound of formula (11) by bromination (process step (iii)). Typical conditions comprise reaction of compound (11) with phosphorous tribromide, in a suitable solvent such as toluene, at reflux for 4 hours.

Compound of formula (6a) where LG is mesylate may be prepared from compound of formula (11) by mesylation (process step (iii)). Typical conditions comprise reaction of compound (11) with methanesulfonyl chloride, in a suitable solvent such as methylethyl ketone, with a suitable base such as triethylamine, at 0° C. to room temperature for 1-4 hours.

The amines of formula (5) may be prepared from the corresponding protected amines of formula (12):

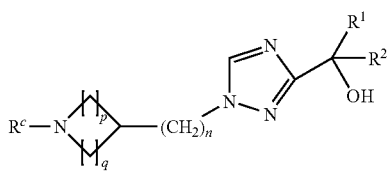
(12)

where $R^c$ represents a suitable protecting group such as tert-butoxycarbonyl or benzyloxycarbonyl.

In a typical procedure, the amine of formula (12) is deprotected using standard methodology for cleaving nitrogen protecting groups such as those found in the text book T. W. Greene, Protective Groups in Organic Synthesis (Wiley-Interscience Publication, 1981).

The amines of formula (12) may be prepared by reacting the corresponding compounds of formula (13):

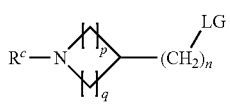
(13)

wherein LG is a suitable leaving group such as bromide or mesylate,
with compounds of formula (14):

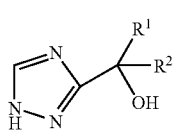
(14)

In a typical procedure, compounds of formula (13) are reacted with compounds of formula (14) in a suitable solvent (e.g. N,N-dimethylformamide, propionitrile, acetonitrile, acetone), in the presence of a suitable base (e.g. potassium carbonate, caesium carbonate, triethylamine, diisopropylethylamine) at a temperature between 70° C. and 150° C., for 5 to 48 hours.

Compounds of formula (13) are commercially available or can be prepared according to methods known to the skilled person.

In particular, the compounds of formula (13) where $R^c$ is tert-butoxycarbonyl, p and q represent 1 or 2, n is 0 and LG is mesylate are commercially available. The compounds of formula (13) where $R^c$ is tert-butoxycarbonyl, p and q are 1, n is 1 and LG is mesylate may be prepared as described in U.S. Pat. Appl. Publ., 2005101586. The compounds of formula (13) where $R^c$ is tert-butoxycarbonyl, p is 1, q is 2, n is 1 and LG is bromide or mesylate are commercially available. Finally, the compounds of formula (13) where $R^c$ is tert-butoxycarbonyl or benzyloxycarbonyl, p and q are 2, n is 1 and LG is bromide are commercially available Compounds of formula (14) may be prepared from the corresponding amides of formula (15):

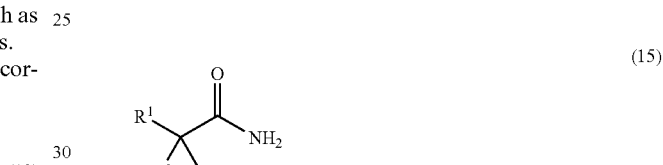
(15)

In a typical procedure, compounds of formula (15) are reacted with N,N-dimethylformamide dimethylacetal at 90° C. for 2 hours. Excess N,N-dimethylformamide dimethylacetal is removed in vacuo and the residue azeotroped with a suitable solvent such as toluene. Hydrazine hydrate is added, followed by glacial acetic acid, and heated at 90° C. for 2 hours.

Compounds of formula (15) may be prepared from the corresponding acids of formula (16):

(16)

In a typical procedure, compounds of formula (16) are reacted with carbonyldiimidazole in a suitable solvent such as dichloromethane or tetrahydrofuran at room temperature for 1 hour, followed by addition of aqueous 0.880 ammonia solution at room temperature for 18 hours.

Compounds of formula (16) and their corresponding single enantiomers, as appropriate, are either commercially available, known in the literature, may be prepared as described in the literature, or by analogous methods to those in the literature. Examples of relevant literature with such information or reference to such information include, but are not limited to: WO2002/053564, WO2006/048225, WO2001/04118, WO2003/057694, WO2004/052857, WO96/33973, Journal of Organic Chemistry, 46(14), 2885-9; 1981, Journal of Organic Chemistry (1961), 26, 1573-7, Chimica Therapeutica (1966) (4), 238-45 and Journal of Medicinal Chemistry, 44(20), 3244-3253; 2001.

For example, the compound of formula (16a):

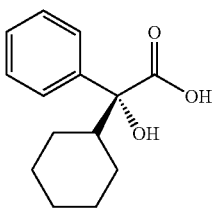

is commercially available as (2R)-2-cyclohexyl-2-hydroxy-2-phenylacetic acid.

Alternatively, compounds of formula (14) may be prepared from the corresponding compounds of formula (17):

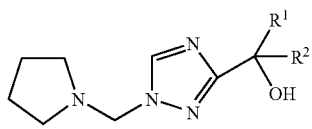

In a typical procedure, compounds of formula (17) are reacted with sodium borohydride in a suitable solvent such as ethanol, at reflux, for 3 hours.

The compounds of formula (17) may be prepared by reacting the compound of formula (18):

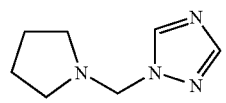

with the compounds of formula (19):

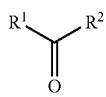

In a typical procedure, the compound of formula (18) is reacted with a suitable base such as n-butyl lithium, in a suitable solvent such as tetrahydrofuran, at a temperature between −78° C. and room temperature for 1 hour, followed by addition of a compound of formula (19) in tetrahydrofuran at a temperature between −78° C. and room temperature for 18 hours.

The compounds of formula (18) may be prepared as described in Tetrahedron: Asymmetry, 8(9), 1491-1500; 1997.

Compounds of formula (19) are either commercially available, may be prepared as described in the literature, or by analogous methods to those described in the literature. Examples of relevant literature with such information include, but are not limited to:

Tetrahedron Letters, 49(11), 1884-1888; 2008; Tetrahedron Letters, 46(44), 7627-7630; 2005

Synthesis, (13), 1970-1978; 2007; Journal of Organic Chemistry, 55(4), 1286-91; 1990; U.S. Pat. No. 5,969,159; Tetrahedron Letters, 47(10), 1649-1651; 2006; Journal of Chemical Research, Synopses, (9), 280-1; 1984; Synthesis, (3), 242-3; 1991; Journal of the Chemical Society, Perkin Transactions 2: Physical Organic Chemistry (1972-1999), (11), 1741-51; 1989; and Synthetic Communications, 34(23), 4249-4256; 2004.

The preparation of compounds of formula (1) may require the protection of potential reactive functionality in addition to those methods already described. In such a case, examples of compatible protecting groups and their particular methods of protection and deprotection are described in "Protecting Groups in Organic Synthesis" by T. W. Greene and P. Wutz (Wiley-Interscience Publication, 1981) or "Protecting groups" by P. J. Kocienski (Georg Thieme Verlag, 1994).

Compounds of formula (1) as well as intermediates for their preparation can be purified and isolated according to various well-known methods, for example crystallisation or chromatography.

Subgroups of compounds of formula (1) containing the following substituents, or combinations of the following substituents, are preferred:

Preferably, A is of formula:

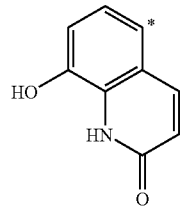

wherein * represent the attachment point of A to the carbon bearing the hydroxyl.

Preferably, X is $(CH_2)_9$ or is of formula:

In a preferred embodiment, X is $(CH_2)_9$.

In another preferred embodiment, X is of formula:

Preferably, Y is of formula:

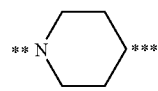

wherein  and * represent the attachment points, ** being linked to X.

Preferably, $R^1$ is phenyl or cyclohexyl.
Preferably, $R^2$ is phenyl.
Preferably, n is 1.
When $R^1$ and $R^2$ are different, the carbon atom bearing these two substituents can be in the (R) or (S) configuration. Preferably, the carbon atom bearing $R^1$ and $R^2$ is in the (R) configuration when $R^1$ and $R^2$ are different.

The compounds of formula (1) wherein:
A is of formula:

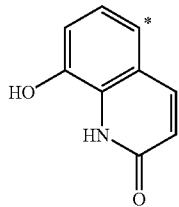

wherein * represent the attachment point of A to the carbon bearing the hydroxy;
X is —(CH$_2$)$_9$— or is of formula:

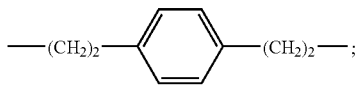

Y is of formula:

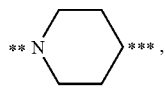

wherein  and * represent the attachment points, ** being linked to X;
n is 1;
R$^1$ is cyclohexyl or phenyl and R$^2$ is phenyl;
or the pharmaceutically acceptable salts thereof, or the pharmaceutically acceptable solvates of said compounds or salts, are further preferred.

The following compounds are more preferred:
5-[(1R)-2-({9-[4-({3-[(R)-cyclohexyl(hydroxy)phenylmethyl]-1H-1,2,4-triazol-1-yl}methyl)piperidin-1-yl]nonyl}amino)-1-hydroxyethyl]-8-hydroxyquinolin-2(1H)-one,
5-[(1R)-2-({9-[4-({3-[(R)-cyclohexyl(hydroxy)phenylmethyl]-1H-1,2,4-triazol-1-yl}methyl)piperidin-1-yl]nonyl}amino)-1-hydroxyethyl]-8-hydroxyquinolin-2(1H)-one naphthalene-1,5-disulfonate salt,
5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one,
5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one naphthalene-1,5-disulfonate salt,
5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one succinate salt,
5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one fumarate salt,
5-[(1R)-2-({9-[4-({3-[cyclohexyl(hydroxy)phenylmethyl]-1H-1,2,4-triazol-1-yl}methyl)piperidin-1-yl]nonyl}amino)-1-hydroxyethyl]-8-hydroxyquinolin-2(1H)-one,
8-hydroxy-5-[(1R)-1-hydroxy-2-({9-[4-({3-[hydroxy(diphenyl)methyl]-1H-1,2,4-triazol-1-yl}methyl)piperidin-1-yl]nonyl}amino)ethyl]quinolin-2(1H)-one, and
8-hydroxy-5-[(1R)-1-hydroxy-2-{[2-(4-{2-[4-({3-[hydroxy(diphenyl)methyl]-1H-1,2,4-triazol-1-yl}methyl)piperidin-1-yl]ethyl}phenyl)ethyl]amino}ethyl]quinolin-2(1H)-one.

5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one is even more preferred.

5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one naphthalene-1,5-disulfonate salt is most preferred.

Pharmaceutically acceptable salts of the compounds of formula (1) include the acid addition and base salts thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:
(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention or a salt thereof and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E.B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of formula (1) contains an alcohol functionality (—OH), an ether thereof, for example, a compound wherein the hydrogen of the alcohol functionality of the compound of formula (1) is replaced by $(C_1-C_6)$alkanoyloxymethyl; and
(ii) where the compound of formula (1) contains a primary or secondary amino functionality (—$NH_2$ or —NHR where R≠H), an amide thereof, for example, a compound wherein, as the case may be, one or both hydrogens of the amino functionality of the compound of formula (1) is/are replaced by $(C_1-C_{10})$alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include
(i) where the compound of formula (1) contains a methyl group, an hydroxymethyl derivative thereof (—$CH_3$→—$CH_2OH$):
(ii) where the compound of formula (1) contains an alkoxy group, an hydroxy derivative thereof (—OR→—OH);
(iii) where the compound of formula (1) contains a tertiary amino group, a secondary amino derivative thereof (—$NR^1R^2$→—$NHR^1$ or —$NHR^2$);
(iv) where the compound of formula (1) contains a secondary amino group, a primary derivative thereof (—$NHR^1$→—$NH_2$);
(v) where the compound of formula (1) contains a phenyl moiety, a phenol derivative thereof (-Ph→—PhOH); and
(vi) where the compound of formula (1) contains an amide group, a carboxylic acid derivative thereof (—$CONH_2$→COOH).

The compounds of formula (1) wherein $R^1$ and $R^2$ are different can exist as stereoisomers. Where structural isomers are interconvertible via a low energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism. In particular, the present invention includes the compounds of formula (1) wherein the triazole moiety may be present as different regio-isomers.

Included within the scope of the present invention are all stereoisomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, nitrogen, such as $^{13}N$ and $^{15}N$, oxygen, such as $^{15}O$, $^{17}O$ and $^{18}O$, and sulphur, such as $^{35}S$.

Certain isotopically-labelled compounds of formula (1), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{15}O$ and $^{13}N$, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (1), the pharmaceutically acceptable salts thereof and/or the pharmaceutically acceptable solvates of said compounds or salts, are valuable pharmaceutically active compounds, which are suitable for the therapy and prophylaxis of numerous disorders in which the $\beta_2$ receptor and/or the muscarinic receptor are involved. In particular, these compounds are useful for the therapy and prophylaxis of numerous disorders in which agonism of the $\beta_2$ receptor and antagonism of the muscarinic receptor may induce benefit, in particular the allergic and non-allergic airways diseases.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol.

Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by a prefilled capsule, blister or pocket or by a system that utilises a gravimetrically fed dosing chamber. Units in accordance with the invention are typically arranged to administer a metered dose or "puff" containing from 1 to 5000 µg of (compound name here), or a salt thereof. The overall daily dose will typically be in the range 1 µg to 20 mg which may be administered in a single dose or, more usually, as divided doses throughout the day.

The compounds of formula (1) are particularly suitable for an administration by inhalation, in particular using a dry powder inhaler.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts thereof and/or pharmaceutically acceptable solvates of said compounds or salts, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough.

The second and more additional therapeutic agents may also be a compound of the formula (1), or pharmaceutically acceptable salts thereof and/or pharmaceutically acceptable solvates of said compounds or salts, or one or more $\beta 2$ agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts thereof and/or pharmaceutically acceptable solvates of said compounds or salts, include, but are by no means limited to:

(a) 5-Lipoxygenase (5-LO) inhibitors or 5-lipoxygenase activating protein (FLAP) antagonists;
(b) Leukotriene antagonists (LTRAs) including antagonists of $LTB_4$, $LTC_4$, $LTD_4$, and $LTE_4$;
(c) Histamine receptor antagonists including H1 and H3 antagonists;
(d) $\alpha_1$- and $\alpha_2$-adrenoceptor agonist vasoconstrictor sympathomimetic agents for decongestant use;
(e) PDE inhibitors, e.g. PDE3, PDE4 and PDE5 inhibitors;
(f) Beta 2 receptor agonists;
(g) muscarinic M3 receptor antagonist or anticholinergic agents;
(h) Theophylline;
(i) Sodium cromoglycate;
(j) COX inhibitors both non-selective and selective COX-1 or COX-2 inhibitors (NSAIDs);
(k) Prostaglandin receptor antagonists and inhibitors of prostaglandin synthase;
(l) Oral and inhaled glucocorticosteroids;
(m) Dissociated agonists of the corticoid receptor (DAGR);
(n) Monoclonal antibodies active against endogenous inflammatory entities;
(o) Anti-tumor necrosis factor (anti-TNF-$\alpha$) agents;
(p) Adhesion molecule inhibitors including VLA-4 antagonists;
(q) Kinin-$B_1$- and $B_2$-receptor antagonists;
(r) Immunosuppressive agents, including inhibitors of the IgE pathway and cyclosporine;
(s) Inhibitors of matrix metalloproteases (MMPs);
(t) Tachykinin $NK_1$, $NK_2$ and $NK_3$ receptor antagonists;
(u) Protease inhibitors such as elastase inhibitors;
(v) Adenosine A2a receptor agonists and A2b antagonists;
(w) Inhibitors of urokinase;
(x) Compounds that act on dopamine receptors, such as D2 agonists;
(y) Modulators of the NF$\kappa\beta$ pathway, such as IKK inhibitors;
(z) modulators of cytokine signalling pathways such as p38 MAP kinase, PI3 kinase, JAK kinase, syk kinase, EGFR or MK-2;
(aa) Agents that can be classed as mucolytics or anti-tussive;
(bb) Agents which enhance responses to inhaled corticosteroids;
(cc) Antibiotics and antiviral agents effective against microorganisms which can colonise the respiratory tract;
(dd) HDAC inhibitors;
(ee) CXCR2 antagonists;
(ff) Integrin antagonists;
(gg) Chemokines;
(hh) Epithelial sodium channel (ENaC) blockers or Epithelial sodium channel (ENaC) inhibitors;
(ii) P2Y2 Agonists and other Nucleotide receptor agonists;
(jj) Inhibitors of thromboxane;
(kk) Inhibitors of $PGD_2$ synthesis and $PGD_2$ receptors (DP1 and DP2/CRTH2);
(ll) Niacin; and
(mm) Adhesion factors including VLAM, ICAM, and ELAM.

According to the present invention, combination of the compounds of formula (1) with:
H3 antagonists;
Muscarinic M3 receptor antagonists;
PDE4 inhibitors;
glucocorticosteroids;
Adenosine A2a receptor agonists;
Modulators of cytokine signalling pathways such as p38 MAP kinase or syk kinase; or
Leukotriene antagonists (LTRAs) including antagonists of $LTB_4$, $LTC_4$, $LTD_4$, and $LTE_4$ are further preferred.

According to the present invention, combination of the compounds of formula (1) with:
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
muscarinic M3 receptor antagonists or anticholinergic agents including in particular ipratropium salts, namely bromide, tiotropium salts, namely bromide, oxitropium salts, namely bromide, perenzepine, and telenzepine are further preferred.

It is to be appreciated that all references herein to treatment include curative, palliative and prophylactic treatment.

The compounds of formula (1) have the ability to interact with the $\beta2$ receptor and cholinergic muscarinic receptors, and thereby have a wide range of therapeutic applications, as described further below, because of the essential role which the $\beta2$ receptor and muscarinic receptors play in the physiology of all mammals.

Therefore, a further aspect of the present invention relates to the compounds of formula (1), or pharmaceutically acceptable salts thereof and/or pharmaceutically acceptable solvates of said compounds or salts, for use in the treatment of diseases, disorders, and conditions in which the $\beta2$ receptor and/or muscarinic receptors are involved. More specifically, the present invention also concerns the compounds of formula (1), or pharmaceutically acceptable salts thereof and/or pharmaceutically acceptable solvates of said compounds or salts, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis;

chronic or acute bronchoconstriction, chronic bronchitis, small airways obstruction, and emphysema;

obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension;

bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis;

acute lung injury; and bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts thereof and/or pharmaceutically acceptable solvates of said compounds or salts, for the manufacture of a drug having a β2 agonist activity and an M3 antagonist activity. In particular, the present inventions concerns the use of the compounds of formula (1), or pharmaceutically acceptable salts thereof and/or pharmaceutically acceptable solvates of said compounds or salts, for the manufacture of a drug for the treatment of diseases and/or conditions involving the beta 2 and muscarinic receptors, in particular the diseases and/or conditions listed above.

As a consequence, the present invention provides a particularly interesting method to treat a mammal, including a human being, with an effective amount of a compound of formula (1), or pharmaceutically acceptable salts thereof and/or pharmaceutically acceptable solvates of said compounds or salts. More precisely, the present invention provides a particularly interesting method for the treatment of a β2-mediated diseases and/or conditions involving the beta 2 and muscarinic receptors, in a mammal, including a human being, in particular the diseases and/or conditions listed above, comprising administering said mammal with an effective amount of a compound of formula (1), its pharmaceutically acceptable salts and/or solvates of said compounds or salts.

The following examples illustrate the preparation of the compounds of formula (1):

FIGURE

FIG. 1/1: PXRD Pattern of Example 2a

PROTOCOLS

For all examples below, the following experimental conditions were used:
Powder X-Ray Diffraction Method (PXRD)

The powder X-ray diffraction pattern was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background cavity silicon wafer specimen mount. The peaks obtained were aligned against a silicon reference standard. The specimen was rotated whilst being irradiated with copper K-alpha$_1$ X-rays (wavelength=1.5406 Ångstroms) with the X-ray tube operated at 40 kV/35 mA. The analyses were performed with the goniometer running in continuous mode set for a 0.2 second count per 0.018° step over a two theta range of 2° to 55°

PREPARATIONS

Preparation 1

(2R)-2-cyclohexyl-2-hydroxy-2-phenylacetamide

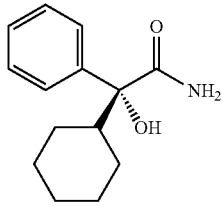

(2R)-2-Cyclohexyl-2-hydroxy-2-phenylacetic acid (preparation 36, 4.87 g, 20.8 mmol) was dissolved in dichloromethane (150 mL) and carbonyldiimidazole (3.37 g, 20.8 mmol) added in one portion. After stirring for 1 hour at room temperature, 0.880 ammonia (21 mL) was added and stirring continued at room temperature for 18 hours. The organic layer was separated, washed with brine (50 mL), dried over magnesium sulphate, filtered and the solvent removed in vacuo to furnish the title compound as a white foam in 92% yield, 4.56 g.

LRMS: APCI ESI m/z 232 [M−H]$^-$ $^1$H NMR (400 MHz, CHLOROFORM-d) δ=0.92 (m, 1H), 1.15 (m, 5H), 1.76 (m, 4H), 2.40 (m, 1H), 5.38 (br.s, 1H), 6.52 (br.s, 1H), 7.28 (m, 1H), 7.37 (m, 2H), 7.62 (m, 2H) ppm.

Preparation 2

(R)-cyclohexyl(phenyl)1H-1,2,4-triazol-3-ylmethanol

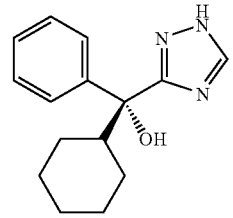

(2R)-2-cyclohexyl-2-hydroxy-2-phenylacetamide (Preparation 1, 4.497 g, 19.27 mmol) was dissolved in N,N-dimethylformamide dimethylacetal (60 ml). After stirring at 90° C. for 2 hours the solvent was removed in vacuo and residue azeotroped with toluene (100 ml) to give a yellow oil. Hydrazine hydrate (1.11 ml, 22.9 mmol) was added followed by glacial acetic acid (90 ml). After stirring at 90° C. for 2 hours the solvent was removed in vacuo and the residue partitioned between ethyl acetate (250 ml) and saturated aqueous sodium bicarbonate solution (250 mL). The organic layer was separated, dried over magnesium sulphate, filtered and the solvent removed in vacuo. The residue was purified by column chromatography on silica gel eluting with ethyl acetate to furnish the title compound as a white solid, in 100% yield, 4.9 g.

LRMS: ESI m/z 256 [M−H]$^-$ $^1$H NMR (400 MHz, CHLOROFORM-d) δ=1.08 (m, 3H), 1.36 (m, 2H), 1.70 (m, 5H), 2.46 (m, 1H), 3.08 (br.s, 1H), 7.23 (m, 1H), 7.34 (m, 2H), 7.65 (m, 2H), 8.00 (s, 1H) ppm.

Enantiomeric excess: 99.3%, calculated using a Chiralpak AS-H Column (250×4.6 mm) eluting with 79% heptane, 31% isopropyl alcohol at a flow rate of 1 ml/min. Retention time of desired (R)-enantiomer 13.61 mins, retention time of undesired (S)-enantiomer 11.31 mins (identified from racemate).

Preparation 3 tert-butyl4-({3-[(R)-cyclohexyl(hydroxy)phenylmethyl]-1H-1,2,4-triazol-1-yl}methyl)piperidine-1-carboxylate

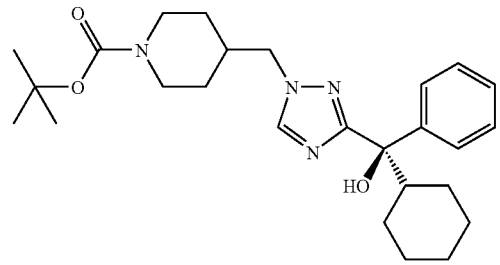

Tert-butyl 4-(bromomethyl)piperidine-1-carboxylate (6.75 g, 24.2 mmol) was dissolved in DMF (62 ml) and (R)-cyclohexyl(phenyl)1H-1,2,4-triazol-3-ylmethanol (Preparation 2, 5.2 g, 20 mmol) added, followed by potassium carbonate (5.58 g, 40.4 mmol). After stirring at 70° C. for 18 hours the solvent was removed in vacuo, and the residue partitioned between ethyl acetate (150 ml) and water (150 mL). The organic layer was separated, dried over magnesium sulphate, filtered and the solvent removed in vacuo. The residue was purified by column chromatography on silica gel eluting with ethyl acetate:heptane, (1:4 to 1:1, by volume) to furnish the title compound as a white foam, in 51% yield, 4.7 g (contains 10% of the other riazole regio-isomer).

LRMS: APCI ESI m/z 487 [M+H+MeOH]+

$^1$H NMR (400 MHz, METHANOL-d$_4$) δ=1.05-1.36 (m, 9H), 1.43 (s, 9H), 1.47-1.75 (m, 5H), 2.09 (m, 1H), 2.38 (m, 1H), 2.72 (m, 2H), 4.08 (m, 4H), 7.17 (m, 1H), 7.26 (m, 2H), 7.58 (d, 2H), 8.03 (s, 1H) ppm.

Alternatively, the title compound was prepared according to the following procedure:

(R)-cyclohexyl(phenyl)1H-1,2,4-triazol-3-ylmethanol (Preparation 2, 3.0 g, 11.7 mmol) was dissolved in acetone (60 mL) and tert-butyl 4-(bromomethyl)piperidine-1-carboxylate (3.24 g, 11.7 mmol) added, followed by cesium carbonate (7.60 g, 23.3 mmol). After stirring at 70° C. for 5 hours, the reaction was allowed to cool to room temperature and stirred for a further 16 hours. The solvent was removed in vacuo, and the residue partitioned between ethyl acetate (50 mL) and water (50 mL). The organic layer was separated, dried over magnesium sulphate, filtered and the solvent removed in vacuo. 100 mg of this residue was dissolved in acetonitrile (0.5 ml) and left to evaporate, almost to dryness, at which point the resulting oil began to crystallise. The remainder of the residue was dissolved in acetonitrile (55 ml) and seeded with the crystalline material obtained above. Crystallisation was allowed to occur over 18 hours and the resulting solid collected by filtration to furnish the title compound as a white solid, in 64% yield, 3.4 g.

LRMS: APCI ESI m/z 487 [M+H+MeOH]+

$^1$H NMR (400 MHz, METHANOL-d$_4$) δ=1.05-1.36 (m, 9H), 1.43 (s, 9H), 1.47-1.75 (m, 5), 2.09 (m, 1H), 2.38 (m, 1H), 2.72 (m, 2H), 4.08 (m, 4H), 7.17 (m, 1H), 7.26 (m, 2H), 7.58 (d, 2H), 8.30 (s, 1H) ppm.

Preparation 4

(R)-cyclohexyl(phenyl)[1-(piperidin-4-ylmethyl)-1H-1,2,4-triazol-3-yl]methanol

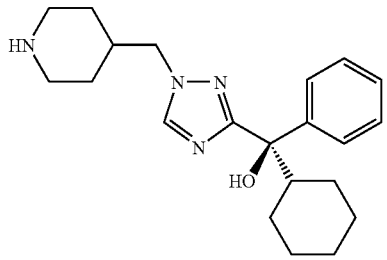

Tert-butyl4-({3-[(R)-cyclohexyl(hydroxy)phenylmethyl]-1H-1,2,4-triazol-1-yl}methyl)piperidine-1-carboxylate (Preparation 3, 5.60 g, 12.3 mmol) was dissolved in DCM (31 ml) and 2M HCl in ether (31 ml, 60 mmol) added. After stirring at room temperature for 5 hours the solvent was removed in vacuo, and the residue partitioned between dichloromethane (200 ml) and saturated aqueous sodium bicarbonate solution (200 ml). The organic layer was separated, dried over magnesium sulphate, filtered and the solvent removed in vacuo to furnish the title compound as a white foam, in 92% yield, 4.03 g (contains 10% of other triazole regio-isomer).

LRMS: APCI ESI m/z 377 [M+Na]+

$^1$H NMR (400 MHz, METHANOL-d$_4$) δ=1.04-1.36 (m, 9H), 1.38-1.57 (m, 2H), 1.58-1.81 (m, 3H), 2.00 (m, 1H), 2.38 (m, 1H), 2.58 (m, 2H), 3.06 (m, 2H), 4.06 (d, 2H), 7.17 (m, 1H), 7.25 (m, 2H), 7.58 (d, 2H), 8.31 (s, 1H) ppm.

Alternatively, the title compound was prepared according to the following procedure:

Tert-butyl 4-({3-[(R)-cyclohexyl(hydroxy)phenylmethyl]-1H-1,2,4-triazol-1-yl}methyl)piperidin-1-carboxylate (Preparation 3a, 2.00 g, 4.40 mmol) was dissolved in dioxane (11 ml) and stirred vigorously to achieve solubilisation. 4M HCl in dioxane (5.54 mL, 22.1 mmol) was then added. After stirring at room temperature for 24 hours the solvent was removed in vacuo, and the residue partitioned between dichloromethane (50 mL) and saturated aqueous sodium bicarbonate solution (50 mL). The organic layer was separated, dried over magnesium sulphate, filtered and the solvent removed in vacuo to furnish the title compound as a colourless oil, in 96% yield, 1.5 g.

LRMS: APCI ESI m/z 377 [M+Na]+

$^1$H NMR (400 MHz, METHANOL-d$_4$) δ=1.04-1.36 (m, 9H), 1.38-1.57 (m, 2H), 1.58-1.81 (m, 3H), 2.00 (m, 1H), 2.38 (m, 1H), 2.58 (m, 2H), 3.06 (m, 2H), 4.06 (d, 2H), 7.17 (m, 1H), 7.25 (m, 2H), 7.58 (d, 2H), 8.31 (s, 1H) ppm.

Preparation 5

Di-tert-butyl{9-[4-({3-[(R)-cyclohexyl(hydroxy)phenylmethyl]-1H-1,2,4-triazol-1-yl}methyl)piperidin-1-yl]nonyl}imidodicarbonate

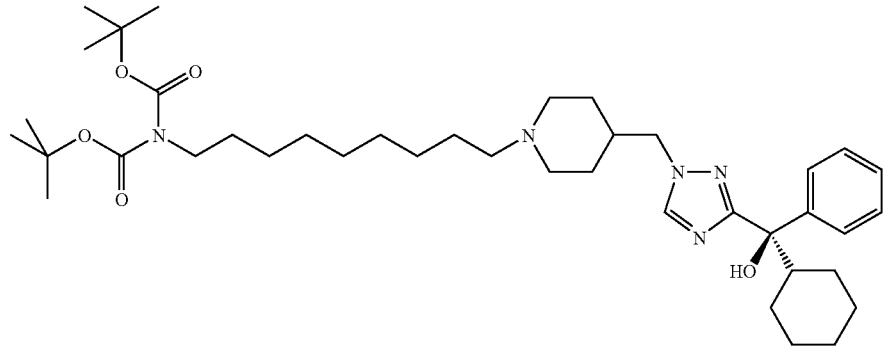

(R)-cyclohexyl(phenyl)[1-(piperidin-4-ylmethyl)-1H-1,2,4-triazol-3-yl]methanol (Preparation 4, 2.00 g, 5.64 mmol) and di-tert-butyl (9-bromononyl)imidodicarbonate (U.S. Pat. No. 4,167,167, 2.38 g, 5.64 mmol) were dissolved in acetonitrile (60 ml) and triethylamine (2.35 ml, 16.9 mmol) added. After stirring at 50° C. for 18 hours, the solvent was removed in vacuo, and the residue purified by column chromatography on silica gel eluting with dichloromethane:methanol:880 ammonia (98:2:0.2, by volume) to furnish the title compound as a clear oil, in 60% yield, 2.6 g (contains 10% of other triazole regio-isomer)

LRMS: APCI ESI m/z 696 [M+H]$^+$ $^1$H NMR (400 MHz, METHANOL-d$_4$) δ=1.14 (m, 4H), 1.25-1.38 (m, 18H) 1.41-1.51 (m, 18H), 1.51-1.75 (m, 6H), 1.99 (m, 2H), 2.14 (m, 2H), 2.42 (m, 2H), 3.06 (m, 2H), 3.55 (m, 2H), 4.09 (m, 2H), 7.16 (m, 1H), 7.26 (m, 2H), 7.58 (m, 2H), 8.32 (m, 1H) ppm.

Preparation 6

(R)-(1-{[1-(9-aminononyl)piperidin-4-yl]methyl}-1H-1,2,4-triazol-3-yl)(cyclohexyl) phenylmethanol

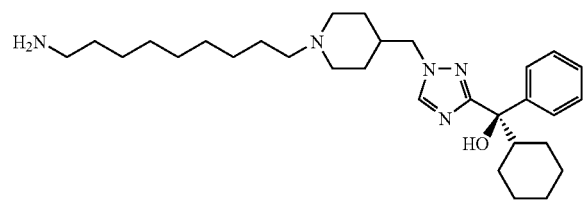

Di-tert-butyl{9-[4-({3-[(R)-cyclohexyl(hydroxy)phenylmethyl]-1H-1,2,4-triazol-1-yl}methyl)piperdin-1-yl]nonyl}imidodicarbonate (Preparation 5, 2.6 g, 3.7 mmol) was dissolved in dichloromethane (15 ml) and hydrogen chloride in diethylether (2M, 15 ml, 30 mmol) added. After stirring at room temperature for 5 hours the solvent was removed in vacuo, the residue was partitioned between dichloromethane (200 ml) and saturated aqueous sodium bicarbonate solution (200 ml). The organic layer was separated, dried over magnesium sulphate, filtered and the solvent removed in vacuo. The residue was purified by column chromatography on silica gel eluting with dichloromethane:methanol:880 ammonia (97.5:2.5:0.25, by volume) to furnish the title compound as a clear oil, in 70% yield, 1.29 g (contains 10% of other triazole regio-isomer).

LRMS: APCI m/z 496 [M+H]$^+$ $^1$H NMR (400 MHz, METHANOL-d$_4$) δ=1.12 (m, 4H), 1.23-1.34 (m, 18H), 1.49 (m, 6H), 1.64 (m, 2H), 1.94 (m, 2H), 2.31 (m, 2H), 2.63 (m, 2H), 2.93 (m, 2H), 4.07 (m, 2H), 7.16 (m, 1H), 7.25 (m, 2H), 7.58 (m, 2H), 8.31 (s, 1H) ppm.

Preparation 7

8-(benzyloxy)-5-[(1R)-1-{[tert-butyl(dimethyl)silyl]oxy}-2-({9-[4-({3-[(R)-cyclohexyl(hydroxy)phenylmethyl]-1H-1,2,4-triazol-1-yl}methyl)piperidin-1-yl]nonyl}amino)ethyl]quinolin-2(1H)-one

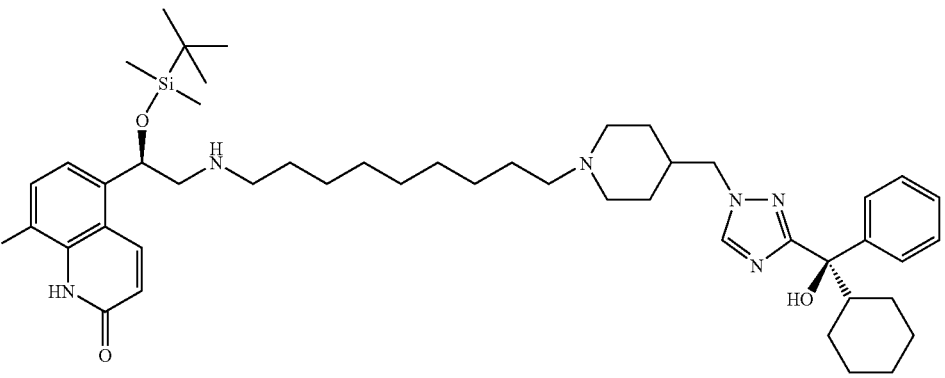

(R)-(1-{[1-(9-aminononyl)piperidin-4-yl]methyl}-1H-1,2,4-triazol-3-yl)(cyclohexyl) phenylmethanol (Preparation 6, 350 mg, 0.706 mg), 8-(benzyloxy)-5-[(1R)-2-bromo-1-{[tert-butyl(dimethyl)silyl]oxy}ethyl]quinolin-2(1H)-one (WO200509286, 345 mg, 0.706 mmol) and sodium hydrogen carbonate (88.9 mg, 1.06 mmol) were combined in acetonitrile (7 mL). After stirring at 90° C. for 72 hours the solvent was removed in vacuo and residue partitioned between dichloromethane (50 ml) and saturated aqueous sodium bicarbonate solution (50 mL). The organic layer was separated, dried over magnesium sulphate, filtered and the solvent removed in vacuo. The residue was purified by column chromatography on silica gel eluting with dichloromethane:methanol:880 ammonia (99:1:0.1 to 95:5:0.5 by volume) to furnish the title compound as a clear glass, in 37% yield, 240 mg (contains 10% of other triazole regio-isomer).

LRMS: APCI ESI m/z 904 [M+H]$^+$ $^1$H NMR (400 MHz, METHANOL-d$_4$) δ=0.07 (s, 3H), 0.37 (s, 3H), 1.17 (s, 9H), 1.37-1.49 (m, 4), 1.52-1.63 (m, 18H), 1.76 (m, 6H), 1.92 (m, 2H), 2.20 (m, 2H), 2.60 (m, 2H), 2.88 (m, 2H), 3.01 (m, 1H), 3.18 (m, 3H), 4.35 (m, 2H), 5.50 (m, 1H), 5.61 (s, 2H), 6.95 (d, 1H), 7.41-7.70 (m, 8H), 7.79 (m, 2H), 7.86 (m, 2H), 8.59 (s, 1H), 8.74 (d, 1H) ppm.

Preparation 8

5-[(1R)-1-{[tert-butyl(dimethyl)silyl]oxy}-2-({9-[4-({3-[(R)-cyclohexyl(hydroxy)phenylmethyl]-1H-1,2,4-triazol-1-yl}methyl)piperidin-1-yl]nonyl}amino)ethyl]-8-hydroxyquinolin-2(1H)-one

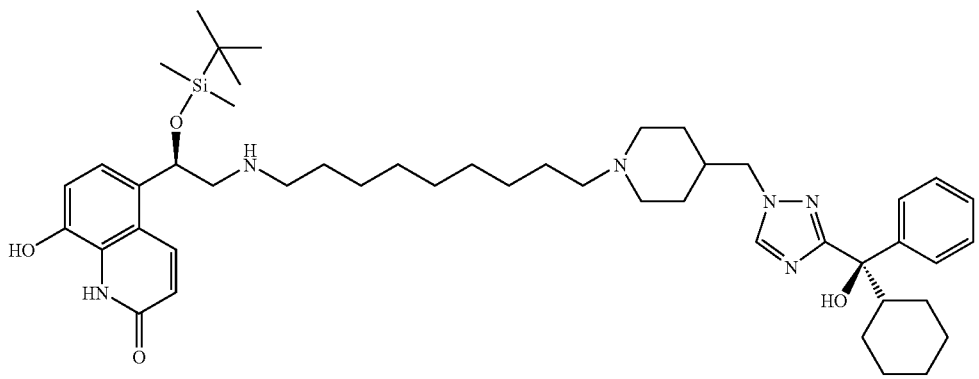

8-(benzyloxy)-5-[(1R)-1-{[tert-butyl(dimethyl)silyl]oxy}-2-({9-[4-({3-[(R)-cyclohexyl(hydroxy)phenylmethyl]-1H-1,2,4-triazol-1-yl}methyl)piperidin-1-yl]nonyl}amino)ethyl]quinolin-2(1H)-one (Preparation 7, 230 mg, 0.255 mmol) was dissolved in ethanol (10 ml) and palladium hydroxide [20 wt. % (dry basis) on carbon (wet)] (5 mg) added followed by ammonium formate (161 mg, 2.55 mmol). After stirring at reflux for 1 hour the reaction mixture was filtered through Arbocel® and the solvent removed in vacuo. The residue was purified by column chromatography on silica gel eluting with dichloromethane:methanol:880 ammonia (97.5:2.5:0.25 to 90:10:1, by volume) to furnish the title compound as a glass, in 87% yield, 180 mg.

LRMS: APCI ESI m/z 813 [M+H]$^+$ $^1$H NMR (400 MHz, METHANOL-$d_4$) δ=0.00 (s, 3H), 0.30 (s, 3H), 1.10 (s, 9H), 1.45-1.94 (m, 28H), 2.21 (m, 3H), 2.58 (m, 3H), 2.85 (m, 2H), 2.95 (m, 1H), 3.17 (m, 3H), 4.29 (m, 2H), 5.42 (m, 1H), 6.85 (d, 1H), 7.14 (d, 1H), 7.32-7.48 (m, 4H), 7.78 (m, 2H), 8.52 (s, 1H), 8.65 (d, 1H) ppm.

Preparation 9

2-{2-[4-(2-Hydroxy-ethyl)-phenyl]-vinyl}-isoindole-1,3-dione

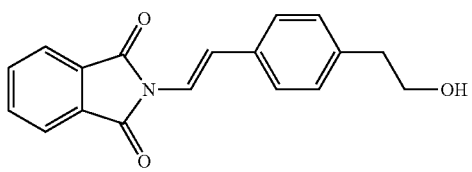

To a solution of 2-(4-bromophenyl)ethanol (48.3 g) in acetonitrile (480 mL) was added diisopropylethylamine (46.6 g), N-vinylphthalimide (43.7 g) and tri-o-tolylphosphine (7.31 g) and the mixture was purged with nitrogen gas three times. Palladium acetate (2.7 g) was added and the mixture was stirred at 90° C. for 21 hr under nitrogen. The reaction was cooled and the precipitated product collected by filtration. The resulting solid was re-dissolved in dichloromethane and ethyl acetate and filtered through silica gel. The filtrate was concentrated in vacuo to give the title compound, 24 g.

$^1$H NMR (400 MHz, CDCl$_3$) δ=2.81-2.84 (t, 2H), 3.82-3.90 (t, 2H), 7.23-7.26 (d, 2H), 7.32-7.26 (d, 1H), 7.40-7.43 (d, 2H), 7.61-7.64 (d, 1H), 7.66-7.78 (d, 2H), 7.86-7.88 (d, 2H) ppm.

Preparation 10

2-{2-[4-(2-Hydroxy-ethyl)-phenyl]-ethyl}-isoindole-1,3-dione

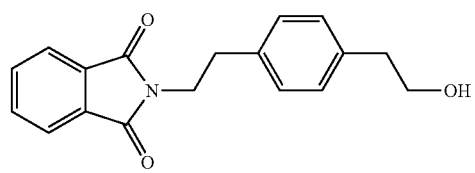

To a stirred solution of 2-{2-[4-(2-Hydroxy-ethyl)-phenyl]-vinyl}-isoindole-1,3-dione (Preparation 9, 10 g) in ethanol and ethyl acetate (350 mL each) was added 30% palladium hydroxide on carbon (1.44 g) followed by ammonium formate (21.5 g). The reaction was heated to 80° C. for 4 hours. Additional palladium hydroxide on carbon (1.44 g) and ammonium formate (21.5 g) were added and the reaction was stirred at 80° C. for 18 hours. The reaction was cooled, filtered through a pad of Arbocel® and rinsed with methanol. The solvent was removed under reduced pressure and the resulting white solid was partitioned between dichloromethane (200 ml) and water (100 ml). The aqueous layer was separated and extracted with further dichloromethane (2×50 mL). The combined organic layers were dried (sodium sulphate) and the solvent removed in vacuo to give the title compound as an off-white solid, 9.11 g.

$^1$H NMR (400 MHz, CDCl$_3$) δ=2.80-2.83 (t, 2H), 2.92-3.00 (t, 2H), 3.82-3.86 (t, 2H), 7.14-7.22 (2×d, 4H), 7.70-7.72 (dd, 2H), 7.82-7.84 (dd, 2H) ppm.

Alternatively, the title compound may be prepared according to the following procedure:

2-{2-[4-(2-hydroxy-ethyl)phenyl]-vinyl}-isoindole-1,3-dione (Preparation 9, 62.0 g, 211.37 mmol) was dissolved in ethyl acetate (1200 mL). To this was added rhodium tris (triphenylphosphine)chloride, (12.7 g, 13.7 mmol) and the mixture hydrogenated at 20 psi, room temperature for 24 hours. The reaction was filtered and concentrated in vacuo. The residue was dissolved in ethyl acetate (1000 mL) and passed through a pad of silica gel, washing with ethyl acetate. The solvent was removed in vacuo to yield a light brown solid which was recrystallised from ethyl acetate:heptane (4:1, by volume) to yield the title compound as an off-white crystalline solid, in 85% yield, 53 g.

$^1$H NMR (400 MHz, CDCl$_3$) δ=2.80-2.83 (t, 2H), 2.92-3.00 (t, 2H), 3.82-3.86 (t, 2H), 3.87-3.96 (t, 2H), 7.14-7.22 (2× d, 4H), 7.70-7.72 (dd, 2H), 7.82-7.84 (dd, 2H) ppm.

Preparation 11

2-{2-[4-(2-Bromo-ethyl)-phenyl]-ethyl}-isoindole-1,3-dione

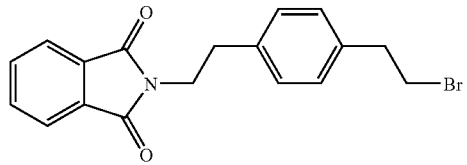

A solution of 2-{2-[4-(2-Hydroxy-ethyl)-phenyl]-ethyl}-isoindole-1,3-dione (Preparation 10, 22.37 g) and phosphorus tribromide (8.20 g) in toluene (500 mL) was refluxed for 4 hours. The mixture was allowed to cool to room temperature, diluted with ethyl acetate (300 mL) and carefully quenched with sodium bisulphite/sodium bicarbonate (1:1) in water (100 mL). The organic layer was separated and washed with further sodium bisulphite/sodium bicarbonate (1:1) in water (100 mL), dried over sodium sulphate and concentrated in vacuo. The resulting solid (24.26 g) was triturated with heptane:tert-butyl methyl ether (100 mL; 9:1, by volume) to give the title compound as a pale green solid, 17.94 g.

$^1$H NMR (400 MHz, CDCl$_3$) δ=2.93-3.00 (t, 2H), 3.07-3.18 (t, 2H), 3.53-3.59 (t, 2H), 3.88-3.94 (t, 2H), 7.13-7.23 (2×d, 4H), 7.70-7.73 (dd, 2H), 7.83-7.85 (dd, 2H) ppm.

Preparation 12

2-[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]-1H-isoindole-1,3(2H)-dione Cyclohexyl-phenyl-(1-piperidin-4-ylmethyl-1H-[1,2,4]triazol-3-yl)-methanol (Preparation 4, 8.2 g, 2.98 mmol), 2-{2-[4-(2-Bromo-ethyl)-phenyl]-ethyl}-isoindole-1,3-dione (Preparation 11, 7.56 g, 21.1 mmol), and triethylamine (13.3 ml, 95.9 mmol) were dissolved in acetonitrile (100 ml). After stirring at 90° C. for 48 hours the solvent was removed in vacuo, and the residue partitioned between dichloromethane (200 ml) and water (200 mL). The organic layer was separated, dried over magnesium sulphate, filtered and the solvent removed in vacuo. The residue was purified by column chromatography on silica gel eluting with dichloromethane:methanol:880 ammonia (98:2:0.2, by volume) and the resulting material then triturated in tert-butyl methyl ether to furnish title compound as a clear solid in 28% yield, 3.4 g.

LRMS: APCI ESI m/z 632 [M+H]$^+$ $^1$H NMR (400 MHz, METHANOL-d$_4$) δ=1.13 (m, 3H), 1.22-1.37 (m, 5H), 1.43 (m, 1H), 1.50-1.74 (m, 5H), 1.94 (m, 1H), 2.03 (m, 2H), 2.38 (m, 1H), 2.52 (m, 2H), 2.73 (m, 2H), 2.90-3.02 (m, 4H), 3.86 (t, 2H), 4.08 (d, 2H), 7.06-7.17 (m, 5H), 7.25 (m, 2H), 7.58 (m, 2H), 7.78 (m, 4H), 8.32 (s, 1H), ppm.

Alternatively, the title compound may be prepared according to the following procedure:

Cyclohexyl-phenyl-(1-piperidin-4-ylmethyl-1H-[1,2,4]triazol-3-yl)-methanol (Preparation 4, 0.40 g, 1.13 mmol) and 2-{2-[4-(2-Bromo-ethyl)-phenyl]-ethyl}-isoindole-1,3-dione (Preparation 11, 0.404 g, 1.13 mmol) and diisopropylethylamine (0.59 ml, 3.38 mmol) were dissolved in methyl ethyl ketone (8 mL). After stirring at 90° C. for 24 hours the reaction was allowed to cool slowly to room temperature. Crystallisation occured and the resulting solid was collected by filtration and dried in vacuo to yield the title compound as a cream coloured solid, in 74% yield, 0.532 g.

LRMS: APCI ESI m/z 632 [M+H]$^+$ $^1$H NMR (400 MHz, METHANOL-d$_4$) δ=1.13 (m, 3H), 1.22-1.37 (m, 5H), 1.43 (m, 1H), 1.50-1.74 (m, 5H), 1.94 (m, 1H), 2.03 (m, 2H), 2.38 (m, 1H), 2.52 (m, 2H), 2.73 (m, 2H), 2.90-3.02 (m, 4H), 3.86 (t, 2H), 4.08 (d, 2H), 7.06-7.17 (m, 5H), 7.25 (m, 2H), 7.58 (m, 2H), 7.78 (m, 4H), 8.32 (s, 1H), ppm.

Alternatively, the title compound was also prepared according to the following procedure:

Methanesulfonic acid 2-{4-[2-(1,3-dioxo-1,3-dihydro-isoindol-2-yl)-ethyl]-phenyl}-ethyl ester (Preparation 35, 20.00 g, 53.56 mmol) was dissolved in acetonitrile (80 mL) and stirred at room temperature. Sodium iodide (16.06 g, 107.12 mmol) was added portionwise and the resulting slurry heated to 80° C. for 18 h. The reaction mixture was cooled to 50° C. and further acetonitrile (80 mL) was added. To this mixture was added cyclohexyl-phenyl-(1-piperidin-4-ylmethyl-1H-[1,2,4]triazol-3-yl)-methanol (Preparation 4, 15.87 g, 53.56 mmol) and diisopropylethylamine (9.79 mL, 56.24 mmol) and heating was continued for 6 hours, then allowed to cool to room temperature. Water (160 mL) was added and the resulting slurry stirred overnight at room temperature. The

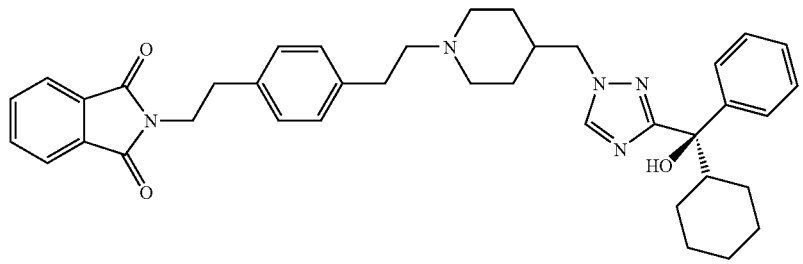

solid was collected by filtration and washed with acetonitrile (5×20 mL), then dried in vacuo at 45° C. for 8 hours to yield the title compound as a brown solid in 68% yield, 20.9 g, LRMS: APCI ESI m/z 632 [M+H]+

¹H NMR (400 MHz, METHANOL-d₄) δ=1.13 (m, 3H), 1.22-1.37 (m, 5H), 1.43 (m, 1H), 1.50-1.74 (m, 5H), 1.94 (m, 1H), 2.03 (m, 2H), 2.38 (m, 1H), 2.52 (m, 2H), 2.73 (m, 2H), 2.90-3.02 (m, 4H), 3.86 (t, 2H), 4.08 (d, 2H), 7.06-7.17 (m, 5H), 7.25 (m, 2H), 7.58 (m, 2H), 7.78 (m, 4H), 8.32 (s, 1) ppm.

Preparation 13

(R)-{1-[(1-{2-[4-(2-aminoethyl)phenyl]ethyl}piperidin-4-yl)methyl]-1H-1,2,4-triazol-3-yl}(cyclohexyl)phenylmethanol

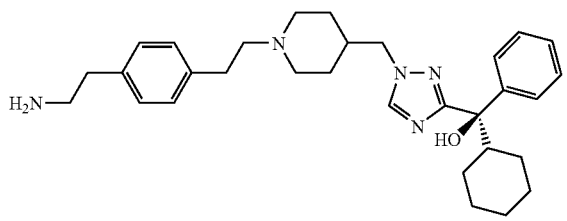

2-[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]-1H-isoindole-1,3(2H)-dione (Preparation 12, 3.4 g, 5.38 mmol) was suspended in ethanol (20 ml) and hydrazine monohydrate (2.61 ml, 53.8 ml) added. After stirring at reflux for 2 hours, the reaction was cooled to room temperature and the precipitate collected by filtration and washed with ethanol (200 ml). The filtrate was concentrated in vacuo to furnish the title compound as a white solid, in 81% yield, 2.57 g.

LRMS: ESI m/z 502 [M+H]+

¹H NMR (400 MHz, METHANOL-d₄) δ=1.04-1.75 (m, 14H), 1.90-2.08 (m, 3H), 2.38 (m, 1H), 2.54 (m, 2H), 2.68-2.78 (m, 4H), 2.84 (m, 2H), 2.99 (m, 2H), 3.96 (d, 2H), 7.09-7.17 (m, 4H), 7.12 (m, 1), 7.25 (m, 2H), 7.59 (m, 2H), 8.31 (s, 1H) ppm.

Preparation 14

8-(benzyloxy)-5-[(1R)-1-{[tert-butyl(dimethyl)silyl]oxy}-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}ethyl]quinolin-2(1H)-one

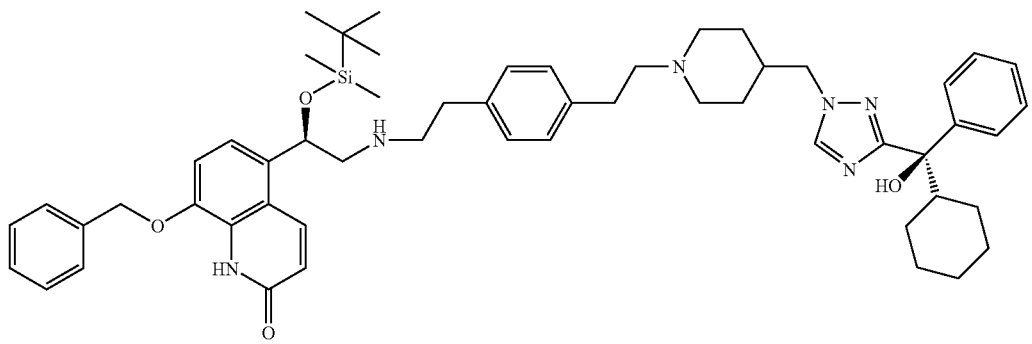

The title compound was prepared from (R)-({-[(1-{2-[4-(2-aminoethyl)phenyl]ethyl}piperidin-4-yl)methyl]-1H-1,2,4-triazol-3-yl}(cyclohexyl)phenylmethanol (Preparation 13, 2.57 g, 5.12 mmol) and 8-(benzyloxy)-5-[(1R)-2-bromo-1-{[tert-butyl(dimethyl)silyl]oxy}ethyl]quinolin-2(1H)-one (WO2005/09286, 2.50 g, 5.12 mmol) using the same method as described in preparation 7 to give a white solid, in 40% yield, 2.3 g.

LRMS: ESI m/z 909 [M+H]+

¹H NMR (400 MHz, METHANOL-d₄) δ=−0.28 (s, 3H), −0.04 (s, 3H), 0.76 (s, 9H), 1.04-1.76 (m, 14H), 1.93 (m, 3H), 2.39 (m, 1H), 2.53 (m, 2H), 2.64-2.79 (m, 5H), 2.79-2.94 (m, 3H), 2.99 (m, 2H), 4.07 (d, 2H), 5.15 (m, 1H), 5.30 (s, 2H), 6.65 (m, 1H), 7.06 (m, 4H), 7.15 (m, 3H), 7.20-7.43 (m, 5H), 7.49 (d, 2H), 7.59 (d, 2H), 8.32 (s, 1H), 8.39 (d, 1H) ppm.

Preparation 15

5-[(1R)-1-{[tert-butyl(dimethyl)silyl]oxy}-2-{[2-(4-{2-[4-({3-[(R)-cyclohexl(hydroxy)phenylmethyl]-1H-1,2,4-triazol-1-yl}methyl)piperidin-1-yl]ethyl}phenyl)ethyl]amino}ethyl]-8-hydroxyquinolin-2(1H)-one

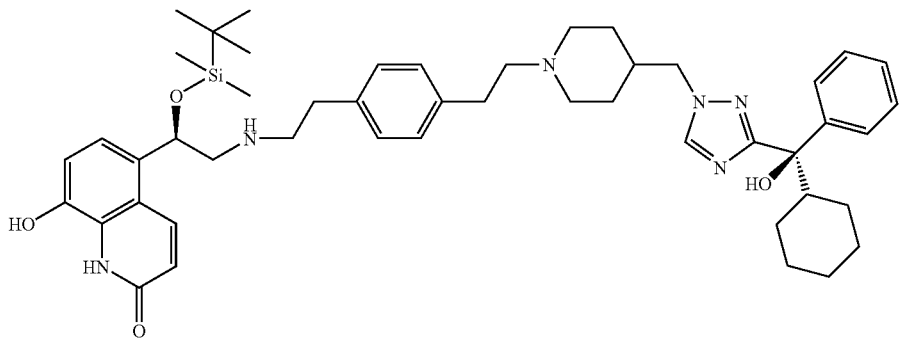

The title compound was prepared from 8-(benzyloxy)-5-[(1R)-1-{[tert-butyl(dimethyl)silyl]oxy}-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}ethyl]quinolin-2(1H)-one (Preparation 14, 2.30 g, 2.81 mmol) using the same method as described in preparation 8, to give a yellow solid, in 91% yield, 2.10 g.

LRMS: ESI m/z 819 [M+H]$^+$ $^1$H NMR (400 MHz, METHANOL-d$_4$) δ=-0.28 (s, 3H), -0.04 (s, 3H), 0.77 (s, 9H), 1.02-1.22 (m, 3H), 1.22-1.51 (m, 6H), 1.51-1.76 (m, 5H), 1.95 (m, 1H), 2.08 (m, 2H), 2.39 (m, 1H), 2.57 (m, 2H), 2.69-2.81 (m, 5H), 2.84-2.94 (m, 3H), 3.07 (m, 2H), 4.08 (d, 2H), 5.13 (m, 1H), 6.62 (d, 1H), 6.91 (d, 1H), 6.99-7.11 (m, 5H), 7.16 (m, 1H), 7.25 (m, 2H), 7.59 (d, 2H), 8.32 (s, 1H), 8.38 (d, 1H) ppm.

Preparation 16

1-(pyrrolidin-1-ylmethyl)-1H-1,2,4-triazole

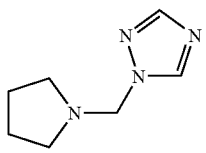

Triazole (10 g, 144.8 mmol) and pyrrolidine (11.3 g, 159.0 mmol) were dissolved ethanol (60 ml) and formaldehyde (37% aqueous solution, 12.9 ml, 159.0 mmol) was added. After stirring at reflux for 4 hours reaction was allowed to stand at room temperature for 18 hours. The solvent was removed in vacuo, and the residue partitioned between dichloromethane (150 ml) and water (80 mL). The aqueous phase was separated and extracted with additional dichloromethane (80 ml). The combined organic layers were washed with brine (100 ml), dried over magnesium sulphate, filtered and the solvent removed in vacuo to furnish the title compound as a yellow oil, in 55% yield, 12.2 g.

$^1$H NMR (400 MHz, CHLOROFORM-d) δ=1.75 (m, 4H), 2.70 (m, 4H), 5.13 (s, 2H), 7.94 (s, 1H), 8.13 (s, 1H) ppm.

Preparation 17

Cyclohexyl(phenyl)[1-(pyrrolidin-1-ylmethyl)-1H-1,2,4-triazol-5-yl]methanol

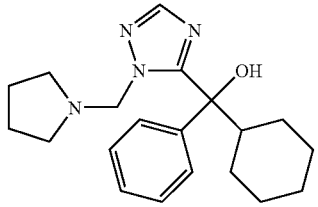

1-(pyrrolidin-1-ylmethyl)-1H-1,2,4-triazole (Preparation 16, 12.0 g, 78.84 mmol) was dissolved in tetrahydrofuran (120 mL) and the solution cooled to −78° C. n-Butyl lithium (2.5M in hexanes, 34.7 ml, 86.7 mmol) was then added dropwise over 30 mins. After warming to room temperature and stirring for 1 hour the reaction mixture was cooled to −78° C. and a solution of cyclohexyl(phenyl)methanone (16.3 g, 86.7 mmol) in tetrahydrofuran (30 mL) added dropwise. After warming to room temperature over 18 hr, water (100 ml) was added and the solvent removed in vacuo. The residue was partitioned with ethyl acetate (200 ml), the aqueous phase separated and re-extracted with ethyl acetate (2×200 ml). The combined organic layers were dried over magnesium sulphate, filtered and the solvent removed in vacuo to furnish the title compound as a yellow oil, in 100% yield, 27.28 g.

$^1$H NMR (400 MHz, CHLOROFORM-d) δ=1.00-1.94 (m, 14H), 2.49 (m 1H), 2.71 (m, 4H), 5.08 (s, 2H), 7.19 (m, 1H), 7.30 (m, 2H), 7.72 (m, 2H), 8.00 (s, 1H) ppm.

Preparation 18

Cyclohexyl(phenyl)1H-1,2,4-triazol-3-ylmethanol

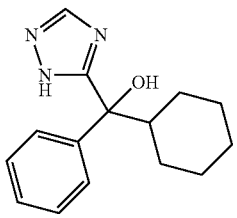

Cyclohexyl(phenyl)[1-(pyrrolidin-1-ylmethyl)-1H-1,2,4-triazol-5-yl]methanol (Preparation 17, 27.28 g, 80.12 mmol) was dissolved in ethanol (400 ml) and sodium borohydride (3.03 g, 80.1 mmol) added portionwise. After stirring at reflux for 3 hours the reaction was left to cool to room temperature over 18 hrs. The solvent was removed in vacuo and the residue purified by column chromatography on silica gel eluting with pentane:ethyl acetate (3:1 to 0:1, by volume) to furnish the title compound as a white foam, in 79% yield, 16.4 g.

LRMS: APCI ESI m/z 256 [M−H]⁻

$^1$H NMR (400 MHz, CHLOROFORM-d) δ=0.90-1.80 (m, 10H), 2.46 (m 1H), 7.25 (m, 1H), 7.33 (m, 2H), 7.67 (m, 2H), 8.00 (s, 1H) ppm.

Preparation 19

Tert-butyl-4-({3-[cyclohexyl(hydroxy)phenylmethyl]-1H-1,2,4-triazol-1-yl}methyl)piperidine-1-carboxylate

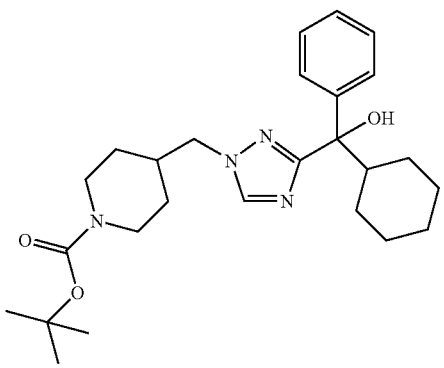

The title compound was prepared from cyclohexyl(phenyl) 1H-1,2,4-triazol-3-ylmethanol (Preparation 18, 500 mg, 1.94 mmol) and tert-butyl4-(bromomethyl)piperidine-1-carboxylate (649 mg, 2.33 mmol) using the same method as described in preparation 3, to give a clear oil, in 47% yield, 415 mg.

LRMS: APCI ESI m/z 381 [M+H]⁺

$^1$H NMR (400 MHz, METHANOL-d₄) δ=1.05-1.45 (m, 9H), 1.43 (s, 9H), 1.52 (m, 2H), 1.67 (3H), 2.09 (m, 1H), 2.38 (m, 1H), 2.72 (m, 2H), 4.08 (m, 4H), 7.17 (m, 1H), 7.26 (m, 2H), 7.58 (d, 2H), 8.30 (s, 1H) ppm.

Preparation 20

Cyclohexyl(phenyl)[1-(piperidin-4-ylmethyl)-1H-1,2,4-triazol-3-yl]methanol

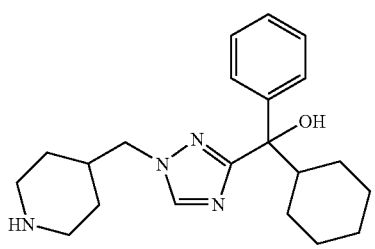

The title compound was prepared from tert-butyl 4-({3-[cyclohexyl(hydroxy)phenylmethyl]-1H-1,2,4-triazol-1-yl}methyl)piperidine-1-carboxylate (Preparation 19, 450 mg, 0.990 mmol) using the same method as described in preparation 4 to give a clear oil, in 91% yield, 320 mg.

LRMS: APCI ESI m/z 378 [M+Na]⁺

$^1$H NMR (400 MHz, METHANOL-d₄) δ=1.04-1.35 (m, 9H), 1.39-1.55 (m, 2H), 1.59-1.75 (m, 3H), 2.03 (m, 1H), 2.38 (m, 1H), 2.5 (m, 2H), 3.01 (m, 2H), 4.05 (d, 2H), 7.15 (m, 1H), 7.27 (m, 2H), 7.58 (d, 2H), 8.31 (s, 1H) ppm.

Preparation 21

Di-tert-butyl{9-[4-({3-[cyclohexyl(hydroxy)phenylmethyl]-1H-1,2,4-triazol-1-yl}methyl)-piperidin-1-yl]nonyl}imidodicarbonate

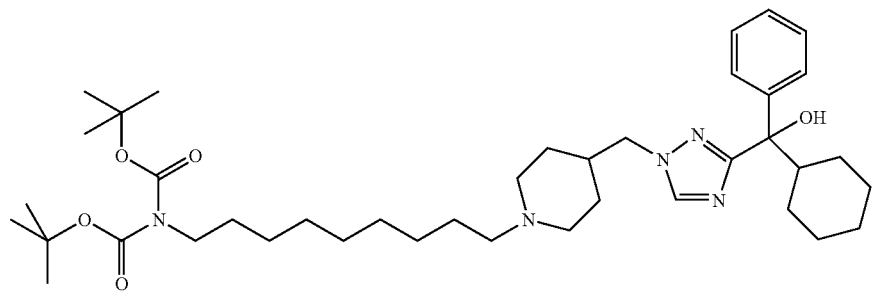

The title compound was prepared from cyclohexyl(phenyl)[1-(piperidin-4-ylmethyl)-1H-1,2,4-triazol-3-yl]methanol (Preparation 20, 300 mg, 0.846 mmol) and di-tert-butyl (9-bromononyl)imidodicarbonate (U.S. Pat. No. 4,167,167, 357 mg, 0.846 mmol) using the same method as described in preparation 5, to give a white foam, in 61% yield, 360 mg.

LRMS: APCI ESI m/z 696 [M+H]+

$^1$H NMR (400 MHz, METHANOL-$d_4$) δ=1.14 (m, 4H), 1.23-1.37 (m, 18H) 1.46-1.60 (m, 24H) 1.68 (m, 2H) 1.96 (m, 2H) 2.33 (m, 2H) 2.95 (m, 2H) 3.55 (m, 2H) 4.07 (m, 2H) 7.16 (m, 1H), 7.26 (m, 2H) 7.58 (m, 2H) 8.31 (s, 1H) ppm.

Preparation 22

(1-{[1-(9-aminononyl)piperidin-4-yl]methyl}-1H-1,2,4-triazol-3-yl)(cyclohexyl)phenylmethanol

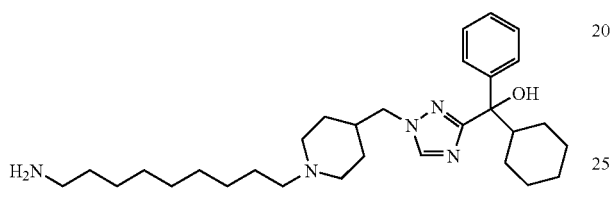

The title compound was prepared from di-tert-butyl{9-[4-({3-[cyclohexyl(hydroxy)phenyl methyl]-1H-1,2,4-triazol-1-yl}methyl)piperidin-1-yl]nonyl}imidodicarbonate (Preparation 21, 360 mg, 0.57 mmol) using the same method as described in preparation 6, to give a clear oil, in 90% yield, 230 mg.

LRMS: APCI m/z 496 [M+H]+

$^1$H NMR (400 MHz, METHANOL-$d_4$) δ=1.12 (m, 4H), 1.22-1.39 (m, 18H), 1.39-1.58 (m, 6H), 1.64 (m, 2H), 1.94 (m, 2H), 2.31 (m, 2H), 2.65 (m, 2H), 2.93 (m, 2H), 4.06 (d, 2H), 7.16 (m, 1H), 7.25 (m, 2H), 7.58 (d, 2H), 8.31 (s, 1H) ppm.

Preparation 23

8-(benzyloxy)-5-[(1R)-1-{[tert-butyl(dimethyl)silyl]oxy}-2-({9-[4-({3-[cyclohexyl(hydroxy)phenyl methyl]-1H-1,2,4-triazol-1-yl}methyl)piperidin-1-yl]nonyl}-amino)ethyl]quinolin-2(1H)-one

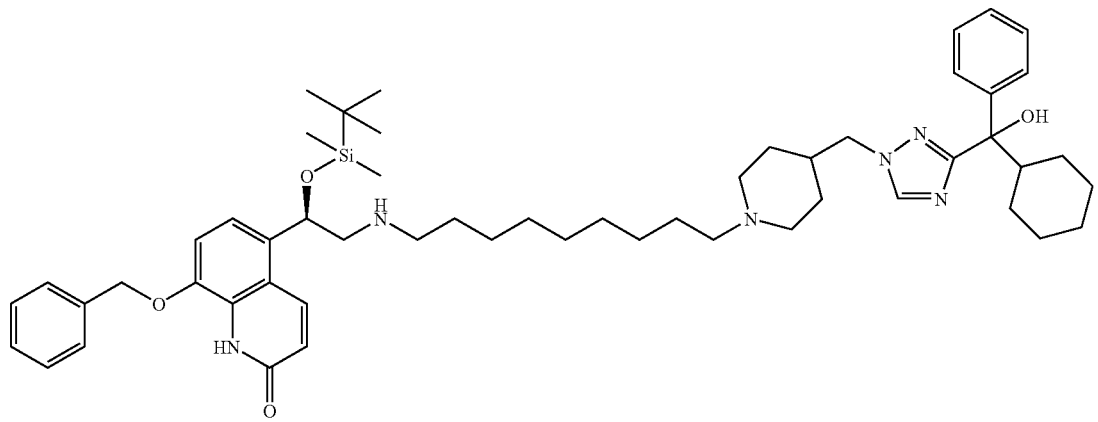

The title compound was prepared from (1-{[1-(9-aminononyl)piperidin-4-yl]methyl}-1H-1,2,4-triazol-3-yl)(cyclohexyl)phenylmethanol (Preparation 22, 150 mg, 0.303 mg) and 8-(benzyloxy)-5-[(1R)-2-bromo-1-{[tert-butyl(dimethyl)silyl]oxy}ethyl]quinolin-2(1H)-one (WO05/09286, 148 mg, 0.303 mmol) using the same method as described in preparation 7, to give a clear oil, in 24% yield, 66 mg.

LRMS: APCI m/z 904 [M+H]+

$^1$H NMR (400 MHz, METHANOL-$d_4$) δ=0.07 (s, 3H), 0.37 (s, 3H), 1.15 (s, 9H), 1.32-1.65 (m, 22H), 1.76 (m, 6H), 1.92 (m, 2H), 2.20 (m, 2H), 2.58 (m, 2H), 2.86 (m, 2H), 3.01 (m, 1H), 3.19 (m, 3H), 4.35 (m, 2H), 5.52 (m, 1H), 5.61 (s, 2H), 6.95 (d, 1H), 7.4-7.69 (m, 8H), 7.79 (m, 2H), 7.86 (m, 2H), 8.59 (s, 1H), 8.74 (d, 1H) ppm.

Preparation 24

5-[(1R)-1-{[tert-butyl(dimethyl)silyl]oxy}-2-({9-[4-({3-[cyclohexyl(hydroxy)phenylmethyl]-1H-1,2,4-triazol-1-yl}methyl)piperidin-1-yl]nonyl}amino)ethyl]-8-hydroxyquinolin-2(1H)-one

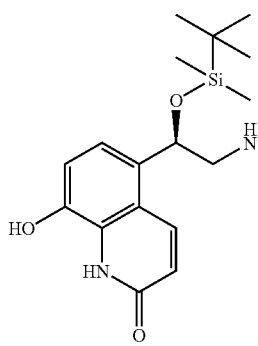

The title compound was prepared from 8-(benzyloxy)-5-[(1R)-1-{[tert-butyl(dimethyl)silyl]oxy}-2-({9-[4-({3-[cyclohexyl(hydroxy)phenylmethyl]-1H-1,2,4-triazol-1-yl}methyl)piperidin-1-yl]nonyl}amino)ethyl]quinolin-2(1H)-one (Preparation 23, 60 mg, 0.066 mmol) using the same method as described in preparation 8, to give a clear glass, in 70% yield, 38 mg.

LRMS: ESI m/z 813 [M+H]+

$^1$H NMR (400 MHz, METHANOL-$d_4$) δ=0.05 (s, 3H), 0.35 (s, 3H), 1.16 (s, 9H), 1.35-1.62 (m, 22H), 1.68-1.85 (m, 6H), 1.85-2.02 (m, 2H), 2.22 (m, 2H), 2.63 (m, 2H), 2.90 (m, 2H), 3.04 (m, 1H), 3.23 (m, 3H), 4.34 (m, 2H), 5.47 (m, 1H), 6.87 (d, 1H), 7.19 (d, 1H), 7.42 (m, 2H), 7.53 (m, 2H), 7.85 (m, 2H), 8.58 (s, 1H), 8.70 (d, 1H) ppm.

Preparation 25

Benzyl 4-({3-[hydroxy(diphenyl)methyl]-1H-1,2,4-triazol-1-yl}methyl)piperidine-1-carboxylate

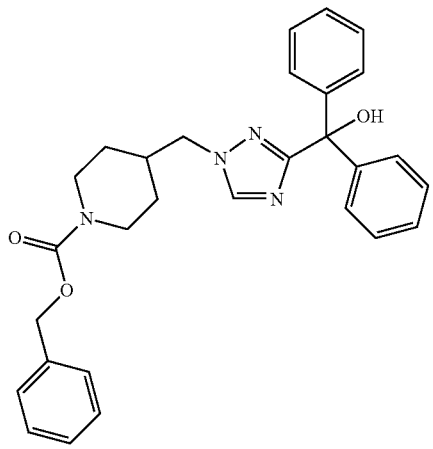

Benzyl 4-(bromomethyl)piperidine-1-carboxylate (5 g, 16 mmol) was dissolved in dimethylformamide (40 ml) and diphenyl-(1H-[1,2,4]triazol-3-yl)-methanol (Tetrahedron: Asymmetry, 8(9), 1491-1500; 1997; 3.35 g, 13.65 mmol) added, followed by potassium carbonate (3.69 g, 26.7 mmol). After stirring at 70° C. for 18 hours the solvent was removed in vacuo, and the residue partitioned between ethyl acetate

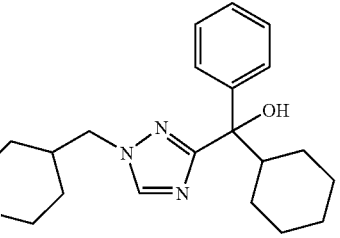

(150 ml) and water (150 mL). The organic layer was separated, dried over magnesium sulphate, filtered and the solvent removed in vacuo to furnish the title compound as a white solid in 81% yield, 5.2 g.

$^1$H NMR (400 MHz, CHLOROFORM-d) δ=1.11-1.40 (m, 5H), 1.50-1.77 (m, 2H), 2.75 (m, 2H), 4.20 (m, 2H), 5.09 (m, 2H), 7.23-7.46 (m, 15H), 8.01 (s, 1H) ppm.

Preparation 26

Diphenyl[1-(piperidin-4-ylmethyl)-1H-1,2,4-triazol-3-yl]methanol

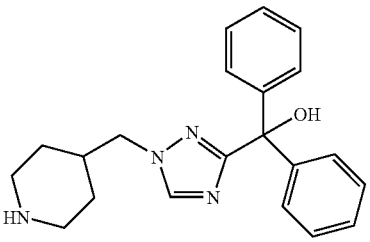

Benzyl 4-({3-[hydroxy(diphenyl)methyl]-1H-1,2,4-triazol-1-yl}methyl)piperidine-1-carboxylate (Preparation 25, 5.2 g, 16.78 mmol) was dissolved in ethanol (300 ml) and ammonium formate (6 g) and palladium hydroxide [20 wt. % (dry basis) on carbon (wet)] (1 g) added. After stirring at reflux for 1 hour the reaction mixture was cooled to room temperature and filtered through Arbocel®. The solvent was removed in vacuo and the residue partitioned between dichloromethane (500 ml) and water (500 mL). The aqueous layer was separated and then basified with aqueous sodium hydroxide solution (2N, 200 ml) and extracted with dichloromethane (500 ml). This organic layer was then dried over magnesium sulphate, filtered and the solvent removed in vacuo. The crude material was recrystallised from acetonitrile to furnish the title compound as a white solid, in 51% yield, 1.9 g.

$^1$H NMR (400 MHz, METHANOL-$d_4$) δ=1.56 (m, 2H), 1.86 (m, 2H), 2.35 (m, 1H), 2.99 (m, 2H), 3.40 (m, 2H), 4.38 (m, 2H), 7.28-7.47 (m, 11H) ppm.

Preparation 27

Di-tert-butyl{9-[4-({3-[hydroxy(diphenyl)methyl]-1H-1,2,4-triazol-1-yl}methyl)piperidin-1-yl]nonyl}imidodicarbonate

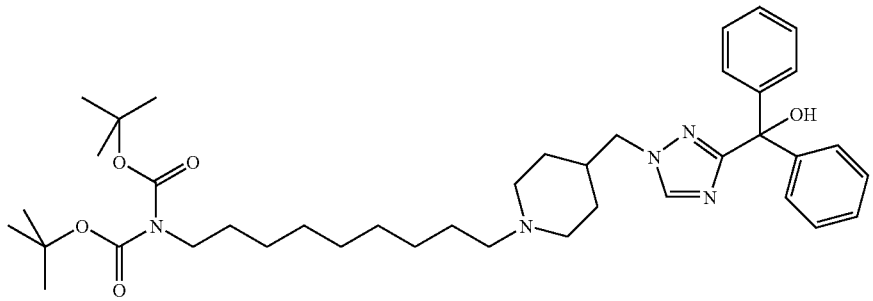

The title compound was prepared from diphenyl[1-(piperidin-4-ylmethyl)-1H-1,2,4-triazol-3-yl]methanol (Preparation 26, 2.00 g, 5.740 mmol) and di-tert-butyl(9-bromononyl)imidodicarbonate (U.S. Pat. No. 4,167,167, 2.42 g, 5.740 mmol) using the same method as described in preparation 5, to give a clear oil, in 43% yield, 1.7 g.

LRMS: APCI ESI m/z 691 [M+H]$^+$ $^1$H NMR (400 MHz, CHLOROFORM-d) δ=1.18-1.35 (m, 11H), 1.41 (m, 3H), 1.49 (s, 18H), 1.57 (m, 4H), 1.94 (m, 3H), 2.38 (m, 2H) 2.96 (m, 2H) 3.54 (m, 2H), 4.00 (m, 2H) 7.22-7.48 (m, 10H), 7.99 (s, 1H) ppm.

Preparation 28

(1-{[1-(9-aminononyl)piperidin-4-yl]methyl}-1H-1,2,4-triazol-3-yl)(diphenyl)methanol

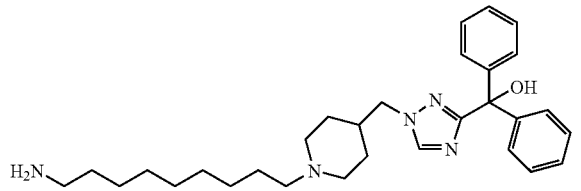

Di-tert-butyl{9-[4-({3-[hydroxy(diphenyl)methyl]-1H-1,2,4-triazol-1-yl}methyl)piperidin-1-yl]nonyl}imidodicarbonate (Preparation 27, 1.7 g, 2.46 mmol) was dissolved ethanol (30 ml) and hydrogen chloride in ether (2M, 30 ml, 60 mmol) added. After stirring at room temperature for 18 hours the solvent was removed in vacuo, and the residue partitioned between dichloromethane (200 ml) and saturated aqueous sodium bicarbonate solution (200 ml). The organic layer was separated, dried over magnesium sulphate, filtered and the solvent removed in vacuo. The residue was purified by column chromatography on silica gel eluting with dichloromethane:methanol:880 ammonia (90:10:1 to 80:20:2, by volume) to furnish the title compound as a white solid, in 60% yield, 725 mg.

$^1$H NMR (400 MHz, METHANOL-d$_4$) δ=1.30 (m, 11H), 1.40-1.62 (m, 7H), 1.93 (m, 3H), 2.28 (m, 2H), 2.61 (m, 2H), 2.94 (m, 2H), 4.09 (m, 2H), 7.20-7.36 (m, 10H), 8.36 (s, 1H) ppm.

Preparation 29

8-(benzyloxy)-5-[(1R)-1-{[tert-butyl(dimethyl)silyl]oxy}-2-({9-[4-({3-[hydroxy(diphenyl)methyl]-1H-1,2,4-triazol-1-yl}methyl)piperidin-1-yl]nonyl}amino)ethyl]quinolin-2(1H)-one

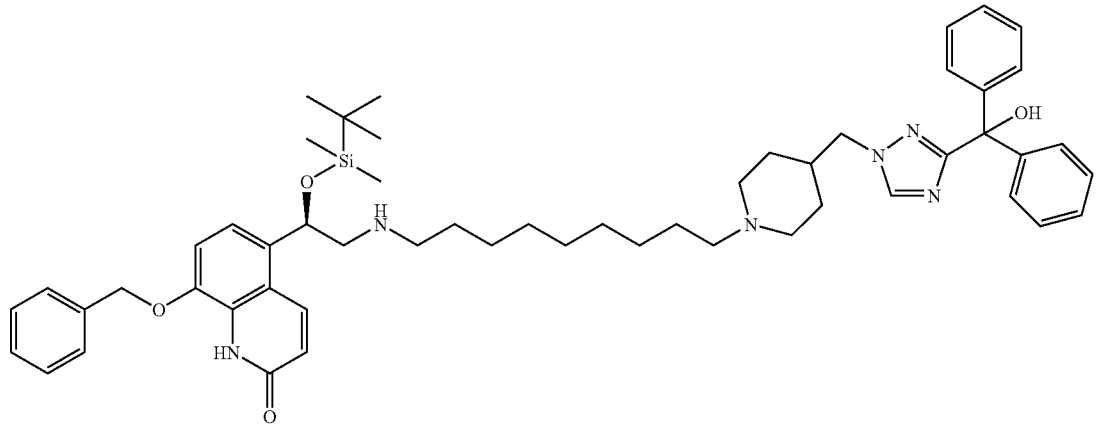

(1-{[1-(9-aminononyl)piperidin-4-yl]methyl}-1H-1,2,4-triazol-3-yl)(diphenyl)methanol (Preparation 28, 710 mg, 1.45 mmol) and 8-(benzyloxy)-5-[(1R)-2-bromo-1-{[tert-butyl(dimethyl)silyl]oxy}ethyl]quinolin-2(1H)-one (WO200509286, 708 mg, 1.45 mmol) were dissolved in dichloromethane (5 ml) and dimethylsulphoxide (100 µl) and diisopropylethylamine (253 µl) added. After stirring in a sealed vessel at 95° C. for 48 hours the solvent was removed in vacuo. The residue was purified by column chromatography on silica gel eluting with dichloromethane:methanol:880 ammonia (90:10:1, by volume) to furnish the title compound as a clear oil, in 38% yield, 500 mg.

LRMS: APCI m/z 898 [M+H]+

Preparation 30

5-[(1R)-1-{[tert-butyl(dimethyl)silyl]oxy}-2-({9-[4-({3-[hydroxy(diphenyl)methyl]-1H-1,2,4-triazol-1-yl}methyl)piperidin-1-yl]nonyl}amino)ethyl]-8-hydroxyquinolin-2(1H)-one

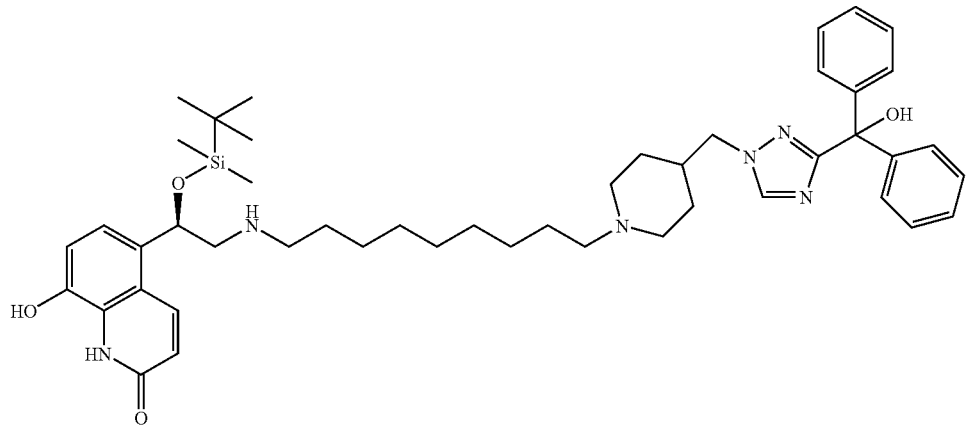

The title compound was prepared from 8-(benzyloxy)-5-[(1R)-1-{[tert-butyl(dimethyl)silyl]oxy}-2-({9-[4-({3-[hydroxy(diphenyl)methyl]-1H-1,2,4-triazol-1-yl}methyl)piperidin-1-yl]nonyl}amino)ethyl]quinolin-2(1H)-one (Preparation 29, 500 mg, 0.056 mmol) using the same method as described in preparation 8, to give a yellow glass, in 59% yield, 267 mg.

LRMS: ESI m/z 807 [M+H]+
1H NMR (400 MHz, METHANOL-d4) δ=0.00 (s, 3H), 0.20 (s, 3H), 1.00 (s, 9H), 1.06-1.82 (m, 18), 2.19 (m, 3H), 2.55 (m, 2H), 2.63 (m, 1H), 2.73 (m, 1H), 3.05 (m, 1H), 3.13 (m, 1H), 3.25 (m, 2H), 4.17 (m, 2H), 5.22 (m, 1H), 6.78 (m, 2H), 7.13-7.48 (m, 7H), 7.58 (m, 4H), 8.17 (m, 1H), 8.50 (m, 1H), ppm.

Preparation 31

2-[2-(4-{2-[4-({3-[hydroxy(diphenyl)methyl]-1H-1,2,4-triazol-1-yl}methyl)piperidin-1-yl]ethyl}phenyl)ethyl]-1H-isoindole-1,3(2H)-dione

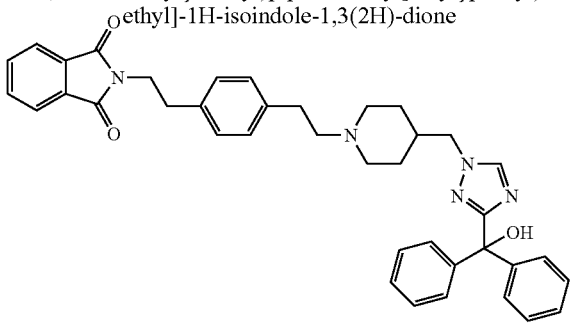

The title compound was prepared from diphenyl[1-(piperidin-4-ylmethyl)-1H-1,2,4-triazol-3-yl]methanol (Preparation 26, 778 mg, 2.23 mmol) and 2-{2-[4-(2-bromoethyl)phenyl]ethyl}-1H-isoindole-1,3(2H)-dione (Preparation 11, 800 mg, 2.23 mmol) using the same method as described in preparation 12, to give a white solid, in 71% yield, 1.00 g.

LRMS: ESI m/z 627 [M+H]+
1H NMR (400 MHz, METHANOL-d4) δ=1.24-2.03 (m, 7H), 2.54 (m, 2H), 2.75 (m, 2H), 2.97 (m, 4H), 3.88 (m, 2H), 3.99 (m, 2H), 7.10 (m, 2H), 7.20 (m, 2H), 7.29 (m, 7H), 7.44 (m, 3H), 7.70 (m, 2H), 7.82 (m, 2H), 7.99 (s, 1H) ppm.

Preparation 32

{1-[(1-{2-[4-(2-aminoethyl)phenyl]ethyl}piperidin-4-yl)methyl]-1H-1,2,4-triazol-3}(diphenyl)methanol

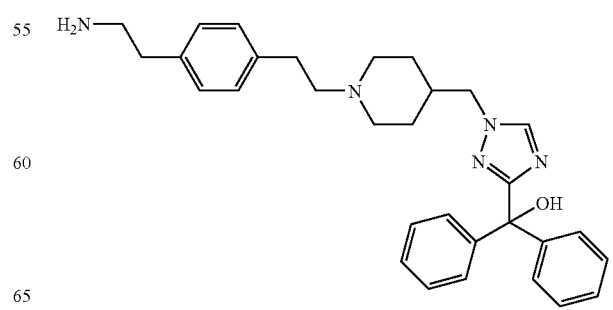

The title compound was prepared from 2-[2-(4-{2-[4-({3-[hydroxy(diphenyl)methyl]-1H-1,2,4-triazol-1-yl}methyl) piperidin-1-yl]ethyl}phenyl)ethyl]-1H-isoindole-1,3(2H)-dione (Preparation 31, 1.0 g, 1.59 mmol) using the same method as described in preparation 13, to give a colourless oil, in 75% yield, 790 mg.

LRMS: ESI m/z 497 [M+H]$^+$ $^1$H NMR (400 MHz, METHANOL-d$_4$) δ=1.37 (m, 2H) 1.58 (m, 2H) 1.93 (m, 1H) 2.05 (m, 2H) 2.54 (m, 2H) 2.73 (m, 4H) 2.83 (m, 2H) 3.02 (m, 2H) 4.09 (d, 2H) 7.13 (m, 4H) 7.26 (m, 6H) 7.33 (m, 4H) 8.38 (s, 1H) ppm.

Preparation 33

8-(benzyloxy)-5-[(1R)-1-{tert-butyl(dimethyl)silyl]oxy}-2-{[2-(4-{2-[4-({3-[hydroxy(diphenyl)methyl]-1H-1,2,4-triazol-1-yl}methyl)piperidin-1-yl] ethyl}phenyl)ethyl]-amino}ethyl]quinolin-2(1H)-one

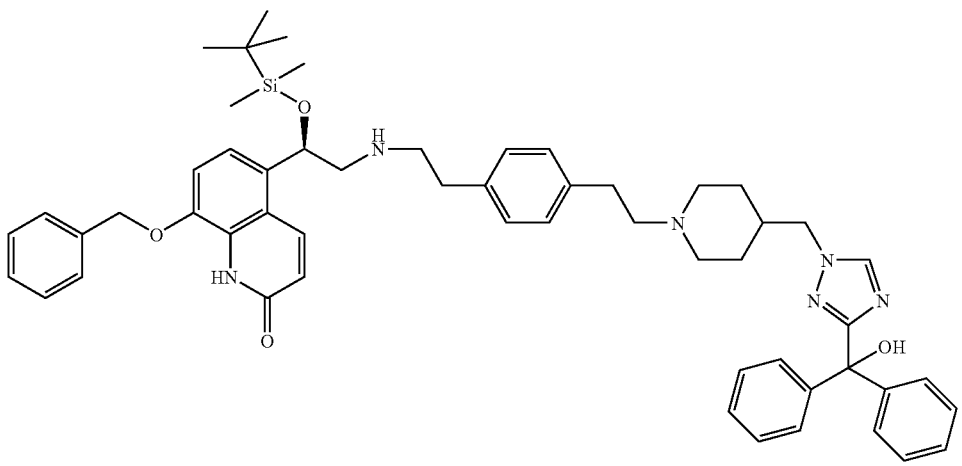

The title compound was prepared from {1-[(1-{2-[4-(2-aminoethyl)phenyl]ethyl}piperidin-4-yl)methyl]-1H-1,2,4-triazol-3-yl}(diphenyl)methanol (Preparation 32, 590 mg, 1.2 mmol) and 8-(benzyloxy)-5-[(1R)-2-bromo-1-{[tert-butyl(dimethyl)silyl]oxy}ethyl]quinolin-2(1H)-one (WO2005/09286, 581 mg, 1.19 mmol) using the same method as described in preparation 7, to give a white solid, in 67% yield, 740 mg.

LRMS: ESI m/z 903 [M+H]$^+$ $^1$H NMR (400 MHz, METHANOL-d$_4$) δ=−0.28 (s, 3H), −0.04 (s, 3H), 0.76 (s, 9H), 1.38 (m, 2H), 1.59 (m, 2H), 1.92 (m, 1H), 2.05 (m, 2H), 2.54 (m, 2H), 2.69-2.94 (m, 8H), 3.03 (m, 2H), 4.11 (m, 2H), 5.15 (m, 1H), 5.32 (s, 2H), 6.65 (d, 1H), 7.08 (m, 4H), 7.16 (m, 2H), 7.27 (m, 6H), 7.35 (m, 7H), 7.50 (m, 2H), 8.40 (s, 2H) ppm.

Preparation 34

5-[(1R)-1-{[tert-butyl(dimethyl)silyl]oxy}-2-{[2-(4-{2-[4-({3-[hydroxy(diphenyl)methyl]-1H-1,2,4-triazol-1-yl}methyl)piperidin-1-yl]ethyl}phenyl)ethyl] amino}ethyl]-8-hydroxyquinolin-2(1H)-one

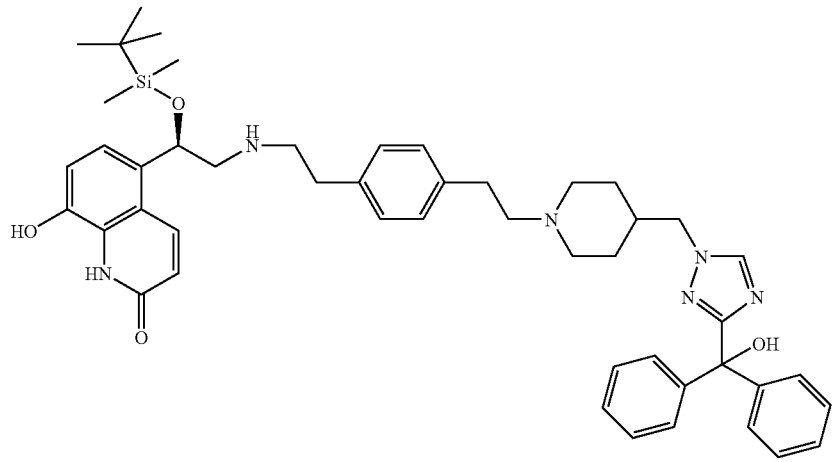

8-(benzyloxy)-5-[(1R)-1-{[tert-butyl(dimethyl)silyl]oxy}-2-{[2-(4-{2-[4-({3-[hydroxy(dephenyl)methyl]-1H-1,2,4-triazol-1-yl}methyl)piperidin-1-yl]ethyl}phenyl)ethyl]amino}ethyl]quinolin-2(1H)-one (Preparation 33, 740 mg, 0.82 mmol), palladium hydroxide [20 wt. % (dry basis) on carbon (wet)](23 mg, 0.164 mmol) and methylcyclohexyldiene (231 mg, 2.46 mmol) were dissolved in MeOH (20 ml). After stirring at 50° C. for 18 hours, additional methylcyclohexyldiene (115.5 mg, 1.23 mmol) was added and stirring continued at 50° C. for a further 18 hours. The reaction mixture was allowed to cool, filtered through Arbocel® and the solvent removed in vacuo to furnish the title compound as yellow solid, in 87% yield, 580 mg.

LRMS: ESI m/z 814 [M+H]$^+$ $^1$H NMR (400 MHz, METHANOL-d$_4$) δ=−0.28 (s, 3H), −0.04 (s, 3H), 0.77 (s, 9H), 1.38 (m, 2H), 1.60 (m, 2H), 1.92 (m, 1H), 2.07 (m, 2H), 2.57 (m, 2H), 2.70-2.96 (m, 8H), 3.05 (m, 2H), 4.10 (m, 2H), 5.14 (m, 1H), 6.59 (d, 1H), 6.92 (d, 1H), 7.08 (m, 4H), 7.15 (m, 1H), 7.25 (m, 6H), 7.35 (m, 4H), 8.33 (d, 1H), 8.40 (s, 1H) ppm.

Preparation 35

Methanesulfonic acid 2-{4-[2-(1,3-dioxo-1,3-dihydro-isoindol-2-yl)-ethyl]-phenyl}-ethyl ester

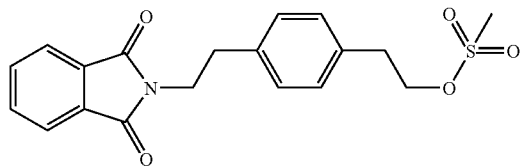

A solution of 2-{2-[4-(2-hydroxy-ethyl)phenyl]-ethyl}-isoindole-1,3-dione (Preparation 10, 21.0 g, 71.25 mmol) in methyl ethyl ketone (315 mL) was cooled to 0° C. Triethylamine (14.9 mL, 106.87 mmol) was added followed by the dropwise addition of methane sulfonyl chloride (6.07 mL, 78.37 mmol). The reaction was stirred at 0-4° C. for 1 hour and then allowed to warm to room temperature. An aqueous solution of potassium carbonate (1M, 210 mL) was added and the mixture stirred. The organic and aqueous layers were separated and the aqueous re-extracted with methyl ethyl ketone (50 mL). The combined organic layers were concentrated to 40 mL by distillation. Tert-butyl methyl ether (300 mL) was slowly added to the hot solution causing crystallisation to occur. The mixture was allowed to cool to room temperature and then allowed to stir for 72 hours. The solid was removed by filtration and washed with tert-butyl methyl ether (3×25 mL). The solid was dried in vacuo at 45° C. for 4 hours to yield the title compound as a light brown solid, in 92% yield, 24.6 g.

$^1$H NMR (400 MHz, CDCl$_3$) δ=2.82 (s, 3H), 2.96-3.02 (m, 4H), 3.89-3.93 (t, 2H), 4.37-4.40 (t, 2H), 7.13-7.23 (2×d, 4H), 7.70-7.72 (dd, 2H), 7.81-7.83 (dd, 2H) ppm.

Preparation 36

(2R)-Cyclohexyl-hydroxy-phenyl-acetic acid

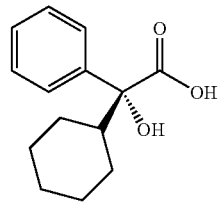

To a slurry of D-tyrosine methyl ester (90.0 g, 460 mmol) in acetonitrile (810 ml) and water (65 ml) was added racemic 2-cyclohexyl-2-hydroxy-2-phenylacetic acid (216.0 g, 921 mmol). The mixture was heated to reflux for 1 hour and then allowed to cool to room temperature overnight. The mixture was further cooled to 4° C. for 4 hours and then filtered, washing with cold acetonitrile (400 ml) to yield a white solid (169.9 g). This solid was partitioned between methyl tert-butyl ether (1.35 L) and 0.5M aqueous hydrochloric acid (765 ml, 1 eq). The organic layer was separated and washed with 0.5M aqueous hydrochloric acid (380 ml, 0.5 eq), dried over sodium sulphate, filtered and the solvent removed in vacuo to furnish the title compound as a white solid, 84.5 g.

LRMS: APCI ESI m/z 233 [M−H]$^−$ $^1$H NMR (400 MHz, DMSO-d6) δ=0.95-1.14 (m, 4H), 1.19-1.29 (m, 1H), 1.32-1.42 (m, 1H), 1.49-1.63 (m, 3H), 1.69-1.78 (m, 1H), 2.11-2.19 (m, 1H), 7.21-7.25 (m, 1H), 7.30-7.34 (m, 2H), 7.57-7.60 (m, 2H), ppm.

EXAMPLES

Example 1

5-[(1R)-2-({9-[4-({3-[(R)-cyclohexyl(hydroxy)phenylmethyl]-1H-1,2,4-triazol-1-yl}methyl)piperidin-1-yl]nonyl}amino)-1-hydroxyethyl]-8-hydroxyquinolin-2(1H)-one

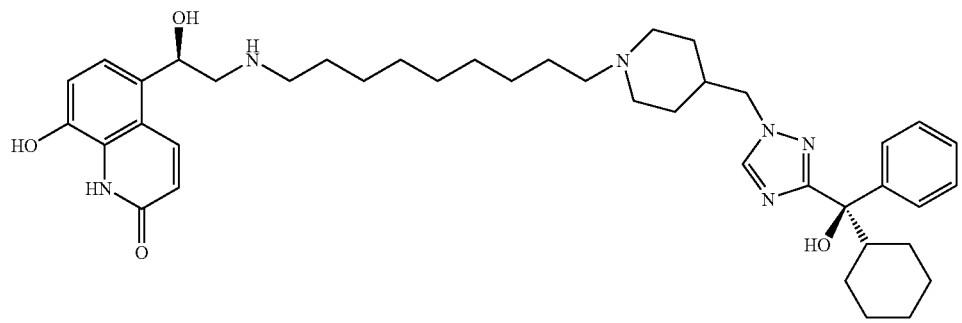

5-[(1R)-1-{[tert-buty(dimethyl)silyl]oxy}-2-({9-[4-({3-[(R)-cyclohexyl(hydroxy)phenylmethyl]-1H-1,2,4-triazol-1-yl}methyl)piperidin-1-yl]nonyl}amino)ethyl]-8-hydroxyquinolin-2(1H)-one (Preparation 8, 13.06 g, 16.06 mmol) was dissolved in methanol (430 ml) and ammonium fluoride (2.97 g, 80.3 mmol) was added. After stirring at 40° C. for 18 hours the solvent was removed in vacuo and the residue partitioned between dichloromethane/methanol (950 ml/50 ml) and saturated aqueous sodium bicarbonate solution (500 mL). The organic layer was separated and the aqueous layer further extracted with dichloromethane/methanol (450 ml/50 ml). The combined organic layers were dried over magnesium sulphate, filtered and the solvent removed in vacuo. The residue was purified by column chromatography on silica gel eluting with dichloromethane:methanol:880 ammonia (90:10:1, by volume) to furnish the title compound as a yellow foam, in 72.3% yield, 8.12 g.

LRMS: ESI m/z 699 [M+H]$^+$ $^1$H NMR (400 MHz, METHANOL-$d_4$) δ=: 1.05-1.77 (m, 28H), 1.98 (m, 3H), 2.35 (m, 3H), 2.75 (m, 2H), 2.95 (m, 4H), 4.09 (m, 2H), 5.24 (m, 1H), 6.65 (d, 1H), 6.95 (d, 1H), 7.15-7.27 (m, 4H), 7.60 (m, 2H), 8.33 (s, 1H), 8.38 (d, 1H) ppm.

Example 1a

5-[(1R)-2-({9-[4-({3-[(R)-cyclohexyl(hydroxy)phenylmethyl]-1H-1,2,4-triazol-1-yl}-methyl)piperdin-1-yl]nonyl}amino)-1-hydroxyethyl]-8-hydroxyquinolin-2(1H)-one; naphthalene-1,5-disulfonate salt

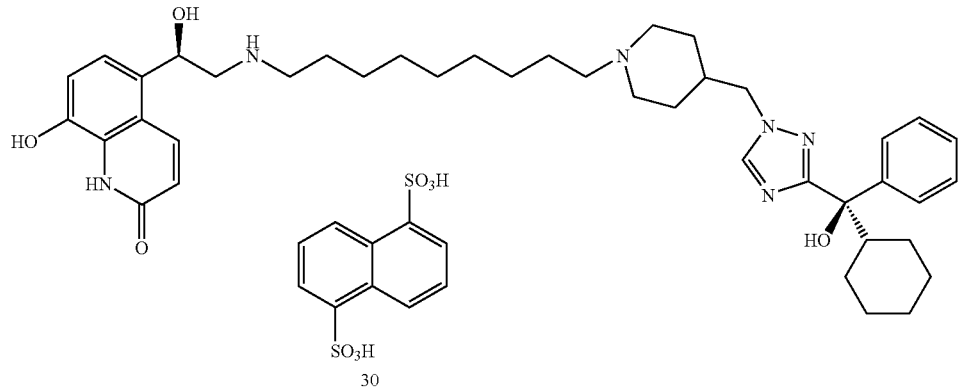

5-[(1R)-2-({9-[4-({3-[(R)-cyclohexyl(hydroxy)phenylmethyl]-1H-1,2,4-triazol-1yl}methyl)piperdin-1-yl]nonyl}amino)-1-hydroxyethyl]-8-hydroxyquinolin-2(1H)-one (Example 1, 2.0 g, 2.86 mmol) was dissolve in methanol (15 ml) and a solution of naphthalene-1,5-disulfonic acid (825.0 mg, 2.86 mmol) in water (3 ml) added dropwise. The mixture was stirred at room temperature overnight. The resulting solid was removed by filtration and dried in vacuo to yield 2.03 g of white solid. 50 mg of this material was treated with methanol:water (70:30 by volume, 1 ml) and the resulting suspension heated to 70° C. and then slow cooled to 20° C. over 24 hours. The solid was recovered by filtration, washing with water and dried in vacuo to yield the title compound as a crystalline white solid, 19 mg.

$^1$H NMR (400 MHz, DMSO-d) δ=: 0.95-1.70 (m, 28H), 1.96-2.29 (m, 3H), 2.71-3.13 (m, 7H), 3.42 (m, 2H), 4.07 (m, 2H), 5.30 (m, 1H), 6.58 (d, 1H), 6.95 (d, 1H), 7.13 (m, 2H), 7.23 (m, 2H), 7.41 (m, 2H), 7.56 (m, 2H), 7.92 (m, 2H), 8.17 (d, 1H), 8.42 (s, 1H), 8.89 (d, 2H) ppm.

Example 2

5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one

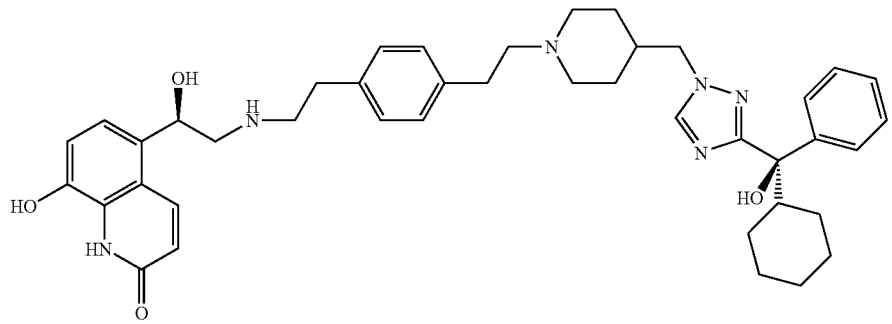

The title compound was prepared from 5-[(1R)-1-{[tert-butyl(dimethyl)silyl]oxy}-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}ethyl]-8-hydroxyquinolin-2(1H)-one (Preparation 15, 2.30 g, 2.81 mmol) using the same method as described in example 1, to give a yellow solid, in 77% yield, 1.40 g.

LRMS: ESI m/z 705 [M+H]$^+$ $^1$H NMR (400 MHz, METHANOL-d$_4$) δ=1.08-1.48 (m, 9H), 1.48-1.81 (m, 5H), 1.94 (m, 1H), 2.08 (m, 2H), 2.38 (m, 1H), 2.54 (m, 2H), 2.66-2.97 (m, 8H), 3.04 (m, 2H), 4.07 (d, 2H), 5.18 (m, 1H), 6.61 (d, 1H), 6.92 (d, 1H), 7.07 (m, 4H), 7.15 (m, 2H), 7.25 (m, 2H), 7.56 (d, 2H), 8.31 (m, 2H), ppm.

Example 2a

5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one; naphthalene-1,5-disulfonate salt

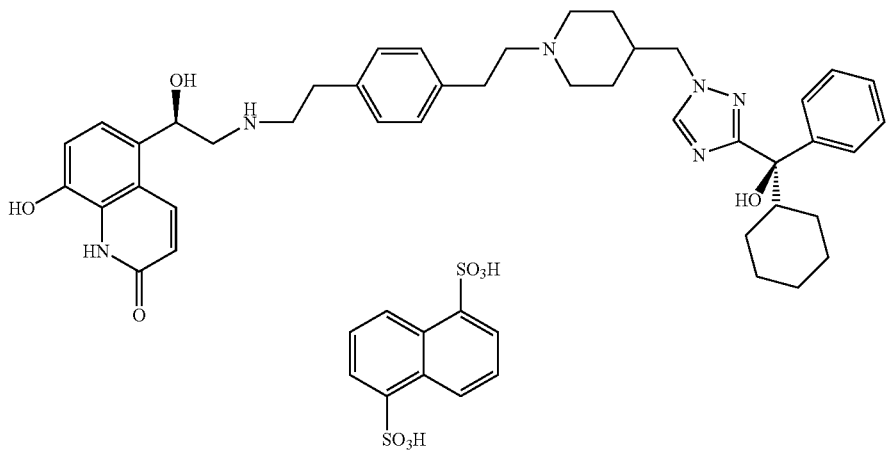

5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one (Example 2, 935 mg, 1.33 mmol) was dissolved in methanol (10 mL). A solution of 1,5-naphthalenedisulphonic acid tetrahydrate (478 mg, 1.33 mmol) in methanol (5 mL) was added and the precipitate that formed was redissolved by adding water (5 mL) and heating. The resulting solution was evaporated in vacuo, re-suspended in methanol (50 mL) and heated to reflux for 30 seconds. The supernatant was decanted from the residue and the residue re-suspended in methanol (50 mL) and heated at reflux with stirring for 4 days. The resulting precipitate was collected by filtration and dried under vacuum to provide the title compound as a colourless crystalline solid, 990 mg. $^1$H NMR (400 MHz, DMSO-d$_6$) δ=0.94-1.49 (m, 8H), 1.50-1.74 (m, 6H), 1.99-2.12 (m, 1H), 2.19-2.27 (m, 1H), 2.83-3.01 (m, 6H), 3.04-3.24 (m, 6H), 3.49-3.59 (m, 2H), 4.05-4.11 (d, 2H), 5.07 (s, 1H), 5.30-5.36 (m, 1H), 6.14-6.19 (d, 1H), 6.57-6.59 (d, 1H), 6.97-6.99 (d, 1H), 7.12-7.19 (m, 6H), 7.24-7.28 (t, 2H), 7.39-7.43 (t, 2H), 7.56-7.58 (d, 2H), 7.94-7.96 (d, 2H), 8.15-8.18 (d, 1H), 8.45 (s, 1H), 8.59-8.74 (bm, 2H), 8.88-8.90 (d, 2H), 9.04-9.19 (bm, 1H), 10.41 (s, 1H), 10.45 (s, 1H) ppm.

The crystalline form produced by the process described above (Form 1) also has the characteristics shown in the corresponding Powder X-ray diffraction pattern of FIG. 1/1.

The main characteristic peaks are at 12.7, 18.1, 21.0, 22.2 and 23.6 degrees 2-theta±0.1 degrees 2-theta and are further given in table 1 below.

TABLE 1

Charateristic PXRD peaks for Example 2a

| Angle (°2θ) | Intensity % |
|---|---|
| 3.166 | 14.4 |
| 6.362 | 14.4 |
| 9.533 | 15.9 |
| 10.568 | 10.4 |
| 10.991 | 13.2 |
| 11.698 | 25.4 |
| 11.976 | 18.6 |
| 12.729 | 81.7 |
| 13.487 | 21.8 |
| 14.306 | 15.9 |
| 15.03 | 26.6 |
| 15.284 | 30.5 |
| 16.044 | 26.5 |
| 16.981 | 55.5 |

TABLE 1-continued

Charateristic PXRD peaks for Example 2a

| Angle (°2θ) | Intensity % |
|---|---|
| 17.206 | 54.3 |
| 17.634 | 46.5 |
| 18.066 | 100 |
| 19.147 | 46.9 |
| 19.459 | 62.3 |
| 20.563 | 46.6 |
| 20.962 | 80.6 |
| 21.204 | 70.2 |
| 22.165 | 84.3 |
| 23.557 | 96.6 |
| 24.709 | 45.6 |
| 25.052 | 43.3 |
| 25.627 | 61.7 |
| 26.362 | 49.2 |
| 27.234 | 41.6 |
| 30.136 | 25.1 |
| 30.626 | 24.3 |
| 31.097 | 22.7 |
| 35.593 | 18.5 |

Example 2b

5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one; succinate salt

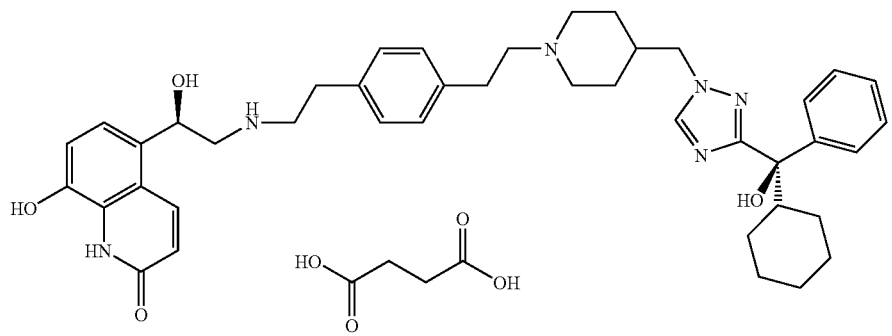

5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one Example 2, 50 mg, 0.07 mmol) was dissolved in methanol (4 mL). A solution of succinic acid (8.4 mg, 0.07 mmol) in methanol (1 mL) was added and the resulting cloudy solution allowed to evaporate on standing overnight. The resulting gum was redissolved in ethanol (2.5 mL) and water (2.5 mL) with heating and then allowed to cool to room temperature with stirring overnight. The resulting precipitate was collected by filtration and dried under vacuum to provide the title compound as a colourless crystalline solid, 28 mg.

$^1$H NMR (400 MHz, DMSO-d$_6$) δ=0.97-1.85 (m, 15H), 1.88-1.93 (m, 2H), 2.19-2.25 (m, 1H), 2.34 (s, 4H), 2.44-2.47 (m, 2H), 2.64-2.68 (m, 2H), 2.71-2.75 (m, 2H), 2.84-2.93 (m, 6H), 4.02 (d, 2H), 5.10-5.13 (m, 1H), 6.52 (d, 1H), 6.93 (d, 1H), 7.07-7.16 (m, 6H), 7.25 (t, 2H), 7.56 (d, 2H), 8.15 (d, 1H), 8.83 (s, 1H) ppm.

Example 2c

5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one; fumarate salt 5-[(1R)-2-{[2-(4-{2-[4-({3-[(R)-cyclohexyl(hydroxy)phenylmethyl]-1H-1,2,4-triazol-1-yl}methyl)piperdin-1-yl]ethyl}phenyl)ethyl]amino}-1-hydroxyethyl]-8-hydroxyquinolin-2(1H)-one (Example 2, 50 mg, 0.07 mmol) was dissolved in methanol (4 mL). A solution of fumaric acid (8.2 mg, 0.07 mmol) in methanol (1 mL) was added and the resulting cloudy solution allowed to evaporate on standing overnight. The resulting gum was redissolved in ethanol (2.5 mL) and water (2.5 mL) with heating and then allowed to cool to room temperature with stirring overnight. The resulting precipitate was collected by filtration and dried under vacuum to provide the title compound as a colourless crystalline solid, 38 mg.

$^1$H NMR (400 MHz, DMSO-d$_6$) δ=0.99-1.84 (m, 15H), 1.91-1.98 (m, 2H), 2.18-2.24 (m, 1H), 2.46-2.49 (m, 2H), 2.65-2.69 (m, 2H), 2.78-2.82 (m, 2H), 2.90-3.02 (m, 6H), 4.03 (d, 2H), 5.19-5.22 (m, 1H), 6.51 (m, 3H), 6.95 (d, 1H), 7.09-7.16 (m, 6H), 7.23-7.27 (m, 2H), 7.56 (d, 2H), 8.18 (d, 1H), 8.39 (s, 1H) ppm.

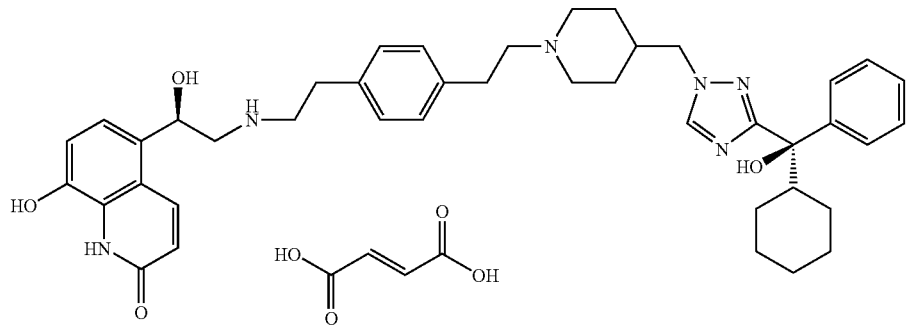

Example 3

5-[(1R)-2-({9-[4-({3-[cyclohexyl(hydroxy)phenylmethyl]-1H-1,2,4-triazol-1-yl}methyl)piperdin-1-yl]nonyl}amino)-1-hydroxyethyl]-8-hydroxyquinolin-2(1H)-one

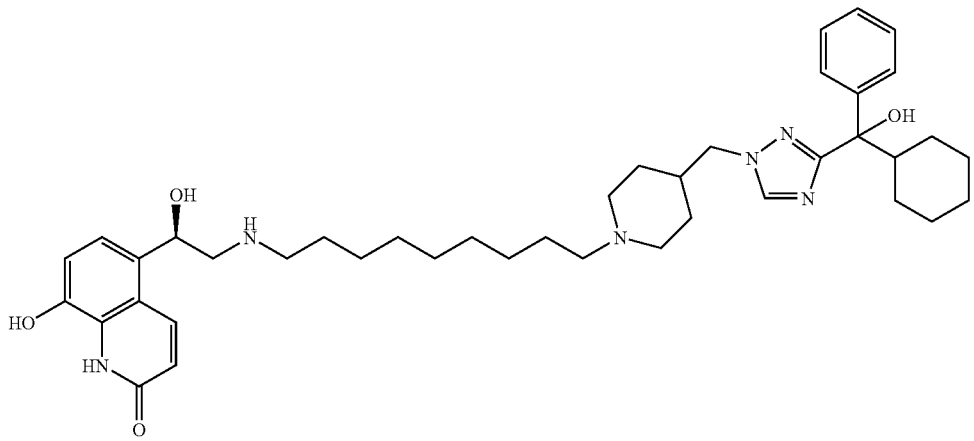

The title compound was prepared from 5-[(1R)-1-{[tert-butyl(dimethyl)silyl]oxy}-2-({9-[4-({3-[cyclohexyl(hydroxy)phenylmethyl]-1H-1,2,4-triazol-1-yl}methyl)piperidin-1-yl]nonyl}amino)ethyl]-8-hydroxyquinolin-2(1H)-one (Preparation 24, 18 mg, 0.022 mmol) using the same method as described in example 1, to give a clear glass, in 65% yield, 10 mg.

LRMS: APCI ESI m/z 699 [M+H]$^+$ $^1$H NMR (400 MHz, METHANOL-$d_4$) δ=: 1.07-1.76 (m, 30H), 1.98 (m, 2H), 2.36 (m, 2H), 2.75 (m, 2H), 2.95 (m, 4H), 4.07 (m, 2H), 5.24 (m, 1H), 6.65 (d, 1H), 6.95 (d, 1H), 7.12-7.28 (m, 4H), 7.58 (m, 2H), 8.31 (s, 1H), 8.37 (d, 1H) ppm.

Example 4

8-hydroxy-5-[(1R)-1-hydroxy-2-({9-[4-({3-[hydroxy(diphenyl)methyl]-1H-1,2,4-triazol-1-yl}methyl)piperdin-1-yl]nonyl}amino)ethyl]quinolin-2(1H)-one

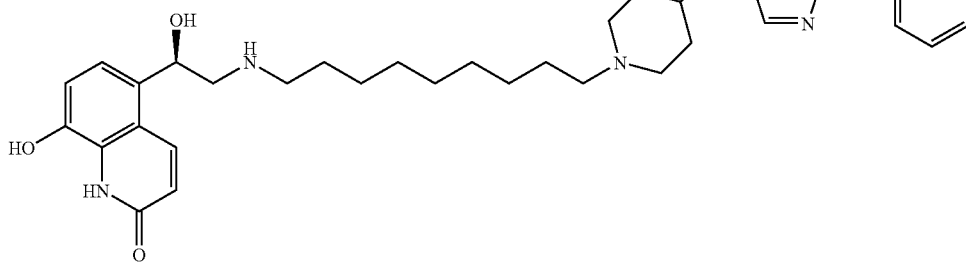

The title compound was prepared from 5-[(1R)-1-{[tert-butyl(dimethyl)silyl]oxy}-2-({9-[4-({3-[hydroxy(diphenyl)methyl]-1H-1,2,4-triazol-1-yl}methyl)piperidin-1-yl]nonyl}amino)ethyl]-8-hydroxyquinolin-2(1H)-one (Preparation 30, 260 mg, 0.322 mmol) using the same method as described in Example 1, to give a yellow glass, in 49% yield, 110 mg.

LRMS: APCI ESI m/z 693 [M+H]$^+$ $^1$H NMR (400 MHz, METHANOL-$d_4$) δ=: 1.24-1.39 (m, 12H), 1.42-1.62 (m, 6H), 1.87-2.03 (m, 3H), 2.34 (m, 2H), 2.74 (m, 2H), 2.93 (m, 4H), 4.07 (m, 2H), 5.24 (m, 1H), 6.63 (d, 1H), 6.95 (d, 1H), 7.17-7.30 (m, 7H), 7.30-7.37 (m, 4H), 8.35 (m, 2H) ppm.

Example 5

8-hydroxy-5-[(1R)-1-hydroxy-2-{[2-(4-{2-[4-({3-[hydroxy(diphenyl)methyl]-1H-1,2,4-triazol-1-yl}methyl)piperidin-1-yl]ethyl}phenyl)ethyl]amino}ethyl]quinolin-2(1H)-one

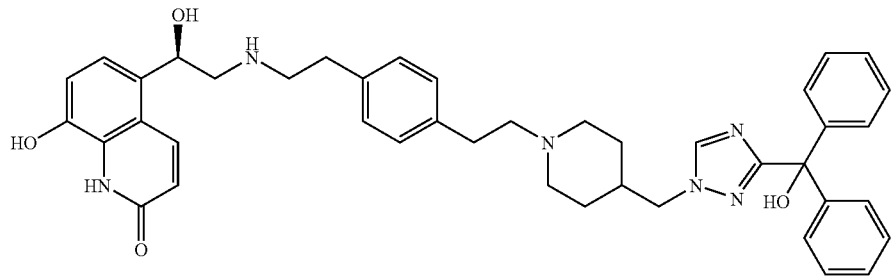

The title compound was prepared from 5-[(1R)-1-{[tert-butyl(dimethyl)silyl]oxy}-2-{[2-(4-{2-(4-({[3-[hydroxy(diphenyl)methyl]-1H-1,2,4-triazol-1-yl}methyl)piperidin-1-yl]ethyl}phenyl)ethyl]amino}ethyl]-8-hydroxyquinolin-2(1H)-one (Preparation 34, 580 mg, 0.71 mmol) using the same method as described in example 1, to give a yellow solid, in 60% yield, 300 mg.

LRMS: APCI ESI m/z 699 [M+H]$^+$ $^1$H NMR (400 MHz, METHANOL-d$_4$) δ=1.37 (m, 2H), 1.58 (m, 2H), 1.91 (m, 1H), 2.07 (m, 2H), 2.54 (m, 2H), 2.82 (m, 8H), 3.04 (m, 2H), 4.11 (m, 2H), 5.18 (m, 1H), 6.62 (d, 1H), 7.05 (m, 4H), 7.15 (m, 1H), 7.25 (m, 6H), 7.34 (m, 4H), 8.33 (d, 1H), 8.38 (s, 1H) ppm.

Binding Affinity Assessment at the Human Recombinant M$_3$ Muscarinic Receptor
Membrane Preparation Cell Pellets from CHO (Chinese Hamster Ovary) cells recombinantly expressing the human muscarinic M$_3$ receptor were homogenised in 20 mM HEPES (pH7.4) and centrifuged at 48000×g for 20 min at 4° C. The pellet was re-suspended in buffer and the homogenisation and centrifugation steps repeated. The resulting pellet was re-suspended in 1 ml buffer per 1 ml original packed cell volume and the homogenisation step repeated. Protein estimation was carried out on the suspension and 1 ml aliquots of ~1 mg/ml frozen at −80° C.

hM$_3$ Competition Binding Assay Protocol

Membranes (5 μg/well) were incubated with $^3$H-NMS (at a concentration 5×K$_D$) plus/minus test compound for 24 hr at RT (room temperature) in a 1 ml polystyrene 96-well deep well block. The final assay volume was 200 μl, comprising of: 20 μl plus/minus test compound; 20 μt, $^3$H-NMS (Perkin Elmer NEN 636) and 160 μl membrane solution. Total Binding was defined with 0.1% DMSO; Non-Specific Binding was defined with 1 μM Atropine. Assay buffer was 20 mM Hepes (pH 7.4).

Once all assay components were added, plates were covered and incubated at room temperature for 24 hrs with shaking. The assay was terminated by rapidly filtering through GF/B Unifilter plates pre-soaked with 0.5% polyethylenimine, using a Packard filtermate harvester, the filter plate was then washed with 3×1 ml 4° C. assay buffer. The filter plates were dried at 45° C. for 1 hour. The bottoms of the filter plates were sealed and 50 μl/well of Microscint '0' added, the top of the plates were sealed with a Topseal. Following 90 mins, the plates were read on an NXT Topcount (1 minute read time per well).

The resulting data was expressed as a percentage of the specific binding (Specific binding=Total binding−Non-Specific Binding). % specific binding versus test compound concentration was plotted to determine an IC$_{50}$ from a sigmoid curve using an in-house data analysis programme. IC$_{50}$ values corrected to Ki values by applying the Cheng-Prussoff equation:

Cheng-Prussoff Equation:

$$K_i = \frac{IC_{50}}{1 + [L]/K_D}$$

where IC$_{50}$ is the concentration of unlabelled drug which inhibits by 50% the specific radioligand binding. [L] is the free radioligand concentrations and K$_D$ and K$_i$ are the equilibrium dissociation constants of the radioligand and unlabelled drug respectively.

Functional Assessment of Agonist Potency and Efficacy Using a Whole cell cAMP Assay in CHO Cells Expressing the hβ$_2$ Receptor
Cell Culture CHO (Chinese Hamster Ovary) cells recombinantly expressing the human adrenergic β$_2$ receptor were maintained in growth media composed of F12:DMEM (Gibco 21331-020) containing 10% Foetal Bovine Serum (FBS: Sigma F4135), 10 μg/ml puromycin (Sigma P8833), 0.1 mg/ml Geneticin G418 (Sigma G7034) and 2 mM L-glutamine (Sigma G7513). The cells were kept in sterile conditions at 37° C., in an atmosphere containing 5% CO$_2$.

hβ$_2$ cAMP Assay Protocol

Cells were harvested for assay when they reached 80-90% confluency using trypsin 0.25% (Sigma T4049) incubated with the cells for 5 min at 37° C. in an atmosphere containing 5% CO$_2$. Detached cells were collected in warmed growth media (composition described above), and re-suspended in assay media (F12:DMEM (Gibco 21331-020) containing 1% Foetal Bovine Serum (FBS: Sigma F4135) and 2 mM L-glutamine (Sigma G7513)) to give a viable cell concentration of 0.25×10$^6$ cells/ml. 100 μl of this suspension was added to each well of a tissue culture treated 96 well view-plate (PerkinElmer 6005181) and the plate incubated in an atmosphere containing 5% CO$_2$ at 37° C. overnight. The following day, cells were washed (4×200 μl, Skatron Skanstacker 300) with Phosphate Buffered Saline (PBS). The plates were then pat dried and the media replaced with 50 μl PBS plus 0.5 mM isobutylmethylxanthine (IBMX) (Sigma I5879) before returning to the incubator for 30 mins. The PBS plate wash procedure was repeated, followed by the addition of 50 μl PBS plus 0.5 mM IBMX and 50 μl PBS plus 2% DMSO and the plates returned to the incubator for 30 mins. Concentration ranges of test compounds were prepared in PBS containing 2% DMSO. The PBS plate wash procedure was repeated, and then 50 μl PBS plus 0.5 mM IBMX was added to the assay plates, followed by the addition of 50 μl of each compound test concentration to the appropriate well. 50 μl per well of 2% DMSO or 200 nM Formoterol was added to the control wells, giving a final assay concentration of 1% DMSO or 100 nM Formoterol. Plates were returned to the incubator for a further 30 mins. At the end of the incubation period the PBS plate wash procedure was repeated a final time as described above. The plates were pat dried and 30 μl per well PBS added followed by 40 μl per well cAMP II ED/Substrate mix and 40 μl per well cAMP II EA-Ab/lysis mix (DiscoverX 90-0034-03). The plates were then incubated in the dark for a minimum of 4 hours at room temperature. The plates were read using a Fusion plate reader (luminescence protocol, each well read for 1 second). Concentration effect curves were plotted and $EC_{50}$ & $E_{max}$ values determined using a 4-parameter sigmoid fit generated using an in-house data analysis programme. Formoterol and salmeterol were run in every assay as reference standards.

It has thus been found that compounds of formula (1) according to the present invention that have been tested in the above assays show $h\beta_2$ receptor agonist activity and $hM_3$ receptor antagonist activity as listed in the table below:

| Example Number | CHO cell $h\beta_2$ cAMP $EC_{50}$ (nM) | CHO cell $h\beta_2$ cAMP $E_{max}$ (%) | CHO cell $hM_3$ binding Ki (nM) |
|---|---|---|---|
| 1 | 14.0 | 103 | 0.570 |
| 2 | 21.6 | 106 | 0.153 |
| 3 | 20.6 | 91 | 0.924 |
| 4 | 13.0 | 90 | 0.505 |
| 5 | 116 | 95 | 2.49 |

The invention claimed is:

1. A compound of formula (1),

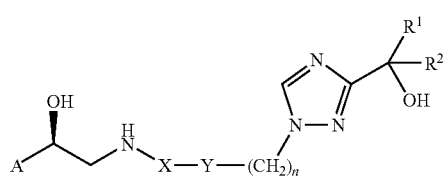
(1)

wherein:
A is selected from:

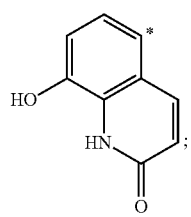

wherein * is the attachment point of A to the carbon bearing the hydroxy;
X is —$(CH_2)_m$— where m is 7 to 12; or
X is:

Y is selected from

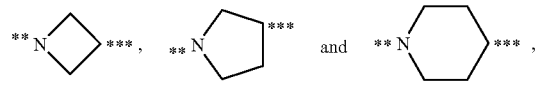

wherein  and * are the attachment points, ** being linked to X;
n is 0 or 1;
$R^1$ is selected from cyclopentyl, cyclohexyl, phenyl, furanyl and thiophenyl; and
$R^2$ is selected from phenyl, furanyl and thiophenyl;
or a pharmaceutically acceptable salt thereof.

2. A compound according to claim 1, or a pharmaceutically acceptable salt thereof, wherein X is —$(CH_2)_9$— or is:

3. A compound according to claim 1, or a pharmaceutically acceptable salt thereof, wherein Y is:

4. A compound according to claim 1, or a pharmaceutically acceptable salt thereof, wherein $R^1$ is phenyl or cyclohexyl.

5. A compound according to claim 1, or a pharmaceutically acceptable salt thereof, wherein $R^2$ is phenyl.

6. A compound according to claim 1, or a pharmaceutically acceptable salt thereof, wherein n is 1.

7. A compound according to claim 1, or a pharmaceutically acceptable salt thereof, wherein:
A is:

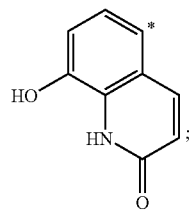

X is —$(CH_2)_9$— or is:

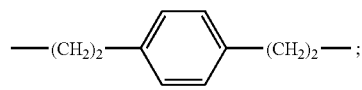

Y is:

n is 1;
R¹ is cyclohexyl or phenyl; and
R² is phenyl.

8. A compound according to claim 1 which is:
5-[(1R)-2-({9-[4-({3-[(R)-cyclohexyl(hydroxy)phenylmethyl]-1H-1,2,4-triazol-1-yl}methyl)piperidin-1-yl]nonyl}amino)-1-hydroxyethyl]-8-hydroxyquinolin-2(1H)-one,
5-[(1R)-2-({9-[4-([3-[(R)-cyclohexyl(hydroxy)phenylmethyl]-1H-1,2,4-triazol-1-yl]methyl)piperidin-1-yl]nonyl}amino)-1-hydroxyethyl]-8-hydroxyquinolin-2(1H)-one;
naphthalene-1,5-disulfonate salt,
5-[(1R)-2-{([2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one,
5-[(1R)-2-{([2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one naphthalene-1,5-disulfonate salt,
5-[(1R)-2-{([2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one succinate salt,
5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one fumarate salt,
5-[(1R)-2-({9-[4-({3-[cyclohexyl(hydroxy)phenylmethyl]-1H-1,2,4-triazol-1-yl}methyl)piperidin-1-yl]nonyl}amino)-1-hydroxyethyl]-8-hydroxyquinolin-2(1H)-one,
8-hydroxy-5-[(1R)-1-hydroxy-2-({9-[4-({3-[hydroxy(diphenyl)methyl]-1H-1,2,4-triazol-1-yl}methyl)piperidin-1-yl]nonyl}amino)ethyl]quinolin-2(1H)-one, or
8-hydroxy-5-[(1R)-1-hydroxy-2-{[2-(4-{(2-[4-({3-[hydroxy(diphenyl)methyl]-1H-1,2,4-triazol-1-yl}methyl)piperidin-1-yl]ethyl}phenyl)ethyl]amino}ethyl]quinolin-2(1H)-one, or a pharmaceutically acceptable salt thereof.

9. 5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one, or a pharmaceutically acceptable salt thereof.

10. A compound according to claim 9 which is 5-[(1R)-2-{[2-(4-{2-[4-({3-[(R)-cyclohexyl(hydroxy)phenylmethyl]-1H-1,2,4-triazol-1-yl}methyl)piperidin-1-yl]ethyl}phenyl)ethyl]amino}-1-hydroxyethyl]-8-hydroxyquinolin-2(1H)-one naphthalene-1,5-disulfonate salt.

11. A pharmaceutical composition comprising at least an effective amount of a compound of claim 1 or a pharmaceutically acceptable salt.

12. A method of treating a disease, disorder or condition in a mammal in need thereof, said method comprising administering to said mammal a therapeutically effective amount of a compound of claim 1, or a pharmaceutically acceptable salt thereof, wherein said disease, disorder or conditions is asthma, chronic or acute bronchoconstriction, bronchitis, small airways obstruction, emphysema, obstructive or inflammatory airways disease, acute lung injury or bronchiectasis.

13. A pharmaceutical composition comprising a combination of a compound of claim 1, or a pharmaceutically acceptable salt thereof, with another therapeutic agent selected from:
(a) 5-Lipoxygenase (5-LO) inhibitors or 5-lipoxygenase activating protein (FLAP) antagonists;
(b) Leukotriene antagonists (LTRAs) including antagonists of $LTB_4$, $LTC_4$, $LTD_4$, and $LTE_4$;
(c) Histamine receptor antagonists including H1 and H3 antagonists;
(d) $\alpha_1$- and $\alpha_2$-adrenoceptor agonist vasoconstrictor sympathomimetic agents for decongestant use;
(e) PDE inhibitors, e.g. PDE3, PDE4 and PDE5 inhibitors;
(f) Beta 2 receptor agonists;
(g) muscarinic M3 receptor antagonist or anticholinergic agents;
(h) Dual compounds active as $\beta_2$ agonists and muscarinic M3 receptor antagonists;
(i) Theophylline;
(j) Sodium cromoglycate;
(k) COX inhibitors both non-selective and selective COX-1 or COX-2 inhibitors (NSAIDs);
(l) Prostaglandin receptor antagonists and inhibitors of prostaglandin synthase;
(m) Oral and inhaled glucocorticosteroids;
(n) Dissociated agonists of the corticoid receptor (DAGR);
(o) Monoclonal antibodies active against endogenous inflammatory entities;
(p) Anti-tumor necrosis factor (anti-TNF-α) agents;
(q) Adhesion molecule inhibitors including VLA-4 antagonists;
(r) Kinin-$B_1$- and $B_2$-receptor antagonists;
(s) Immunosuppressive agents, including inhibitors of the IgE pathway and cyclosporine;
(t) Inhibitors of matrix metalloproteases (MMPs);
(u) Tachykinin $NK_1$, $NK_2$ and $NK_3$ receptor antagonists;
(v) Protease inhibitors such as elastase inhibitors;
(w) Adenosine A2a receptor agonists and A2b antagonists;
(x) Inhibitors of urokinase;
(y) Compounds that act on dopamine receptors, such as D2 agonists;
(z) Modulators of the NFκ pathway, such as IKK inhibitors;
(aa) modulators of cytokine signalling pathways such as p38 MAP kinase, PI3 kinase, JAK kinase, syk kinase, EGFR or MK-2;
(bb) Agents that can be classed as mucolytics or antitussive;
(cc) Agents, which enhance responses to inhaled corticosteroids;
(dd) Antibiotics and antiviral agents effective against micro-organisms which can colonise the respiratory tract;
(ee) HDAC inhibitors;
(ff) CXCR2 antagonists;
(gg) Integrin antagonists;
(hh) Chemokines;
(ii) Epithelial sodium channel (ENaC) blockers or Epithelial sodium channel (ENaC) inhibitors;
(jj) P2Y2 Agonists and other Nucleotide receptor agonists;
(kk) Inhibitors of thromboxane;
(ll) Inhibitors of $PGD_2$ synthesis and $PGD_2$ receptors (DP1 and DP2/CRTH2);
(mm) Niacin; and
(nn) Adhesion factors including VLAM, ICAM, and ELAM.

14. A method according to claim 12 wherein said asthma is selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

15. A method according to claim 12 wherein said obstructive or inflammatory airways disease is selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension.

16. A method according to claim 12 wherein said bronchitis is selected from the group consisting of chronic bronchitis, acute bronchitis, acute laryngotracheal bronchitis, arachidic bronchitis, catarrhal bronchitis, croupus bronchitis, dry bronchitis, infectious asthmatic bronchitis, productive bronchitis, staphylococcus bronchitis, streptococcal bronchitis and vesicular bronchitis.

17. A method according to claim 12 wherein said bronchiectasis is selected from the group consisting of cylindric bronchiectasis, sacculated bronchiectasis, fusiform bronchiectasis, capillary bronchiectasis, cystic bronchiectasis, dry bronchiectasis and follicular bronchiectasis.

18. The method according to claim 12 wherein said disease, disorder or condition is asthma or chronic obstructive pulmonary disease (COPD).

* * * * *